US008245705B2

(12) United States Patent
Li

(10) Patent No.: US 8,245,705 B2

(45) Date of Patent: Aug. 21, 2012

(54) INHALER

(76) Inventor: Jianhe Li, Nottingham Nottinghamshire (GB)

( * ) Notice: Subject to any disclaimer, the term of this patent is extended or adjusted under 35 U.S.C. 154(b) by 1025 days.

(21) Appl. No.: 12/280,222

(22) PCT Filed: Feb. 19, 2007

(86) PCT No.: PCT/GB2007/050071

§ 371 (c)(1), (2), (4) Date: Aug. 21, 2008

(87) PCT Pub. No.: WO2007/096667

PCT Pub. Date: Aug. 30, 2007

(65) Prior Publication Data

US 2009/0064997 A1 Mar. 12, 2009

(30) Foreign Application Priority Data

Feb. 21, 2006 (GB) .................................. 0603377.3

(51) Int. Cl.
*A61M 11/00* (2006.01)

(52) U.S. Cl. ......... 128/200.23; 128/203.12; 128/203.15; 128/203.23; 128/203.24; 128/203.25; 128/200.14; 128/200.24

(58) Field of Classification Search ............. 128/203.12, 128/203.15, 203.23, 203.24, 203.25, 200.14, 128/200.23, 200.24
See application file for complete search history.

(56) References Cited

U.S. PATENT DOCUMENTS

| | | | | |
|---|---|---|---|---|
| 5,161,524 | A | | 11/1992 | Evans |
| 5,239,992 | A | | 8/1993 | Bougamont et al. |
| 5,287,850 | A | | 2/1994 | Haber et al. |
| 5,388,572 | A | | 2/1995 | Mulhauser et al. |
| 5,408,994 | A | | 4/1995 | Wass et al. |
| 5,511,540 | A | | 4/1996 | Bryant et al. |
| 5,617,845 | A | * | 4/1997 | Poss et al. ............... 128/203.15 |
| 5,875,776 | A | | 3/1999 | Vaghefi |
| 6,012,454 | A | | 1/2000 | Hodson et al. |
| 6,029,662 | A | | 2/2000 | Marcon |
| 6,044,841 | A | * | 4/2000 | Verdun et al. ............ 128/200.18 |
| 6,098,609 | A | | 8/2000 | Ishizuka |
| 6,098,619 | A | | 8/2000 | Britto et al. |
| 6,152,130 | A | | 11/2000 | Abrams et al. |

(Continued)

FOREIGN PATENT DOCUMENTS

EP 0069715 A1 1/1983

(Continued)

OTHER PUBLICATIONS

Adherence and compliance in the management of ashtma: 1, Br J Nurs. Nov. 26-Dec. 9, 1998;7(21):1313-5.*

(Continued)

*Primary Examiner* — Loan Thanh
*Assistant Examiner* — Bradley Philips
(74) *Attorney, Agent, or Firm* — Brooks Kushman P.C.

(57) ABSTRACT

The invention provides an inhaler for dispensing medicament. The inhaler comprises auxiliary energy provision means for providing auxiliary energy for aerosolizing medicament; energy release means for releasing auxiliary energy from the auxiliary energy provision means; feed means for feeding a dose of medicament, characterized in that the inhaler comprises control means for controlling a time interval between aerosolization of the medicament and a user's inhalation. The inhaler is operable, in use, to aerosolize medicament using the auxiliary energy, and harness the user's inhalation to deliver the aerosolized medicament to the user.

12 Claims, 15 Drawing Sheets

U.S. PATENT DOCUMENTS

Figure 1A:
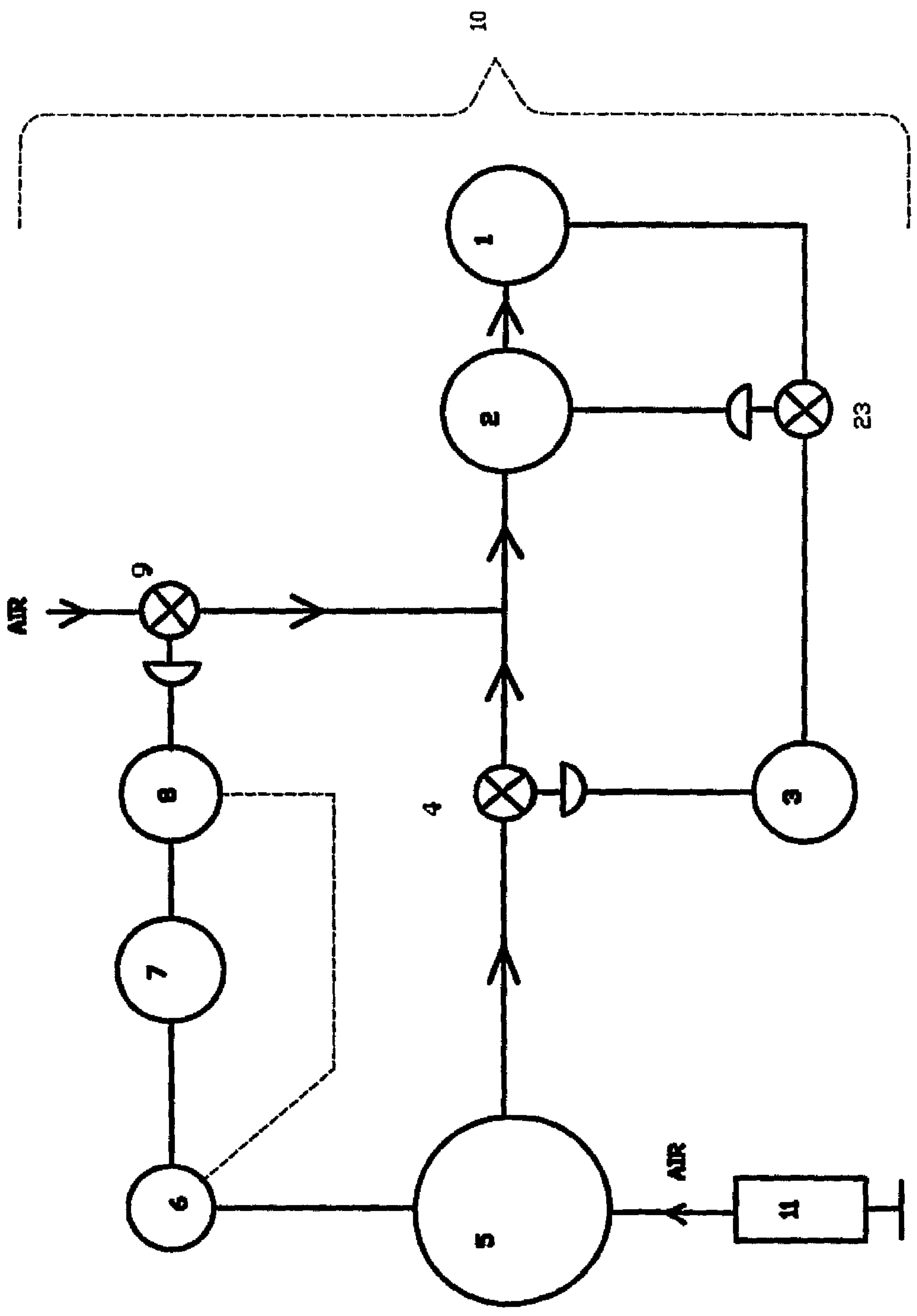

| | | | | |
|---|---|---|---|---|
| 6,260,549 | B1 | 7/2001 | Sosiak | |
| 6,273,085 | B1 | 8/2001 | Eisele | |
| 6,555,381 | B2 | 4/2003 | Baugh et al. | |
| 6,561,186 | B2 | 5/2003 | Casper et al. | |
| 6,655,381 | B2 | 12/2003 | Keane et al. | |
| 6,752,152 | B2 * | 6/2004 | Gale et al. | 128/204.26 |
| 6,769,601 | B2 | 8/2004 | Haikarainen et al. | |
| 6,901,929 | B2 | 6/2005 | Burr et al. | |
| 6,971,384 | B2 | 12/2005 | Gieschen et al. | |
| 2002/0005933 | A1 | 1/2002 | Imafuku | |
| 2003/0079743 | A1 | 5/2003 | Genova et al. | |
| 2004/0050385 | A1 | 3/2004 | Bonney et al. | |
| 2004/0187868 | A1 | 9/2004 | Hochrainer et al. | |
| 2005/0005933 | A1 | 1/2005 | Seppala et al. | |

FOREIGN PATENT DOCUMENTS

| | | | |
|---|---|---|---|
| EP | 0911048 | A2 | 4/1999 |
| GB | 1562098 | | 3/1980 |
| GB | 2405799 | A | 3/2005 |
| WO | 9204068 | A1 | 3/1992 |
| WO | 9207599 | A1 | 5/1992 |
| WO | 9512428 | A1 | 4/1994 |
| WO | 0021598 | A1 | 4/2000 |
| WO | 0100262 | A1 | 1/2001 |
| WO | 0158514 | A1 | 8/2001 |
| WO | 0185245 | A1 | 11/2001 |
| WO | 03045483 | A2 | 6/2003 |
| WO | 03082389 | A1 | 10/2003 |
| WO | 03095005 | A1 | 11/2003 |
| WO | 2004103445 | A1 | 12/2004 |

OTHER PUBLICATIONS

Smith et al. "The Inhalers of the Future? A Review of dry Powder Devices on the Market Today", Pulmonary Pharmacology & Therapeutics 2003, vol. 16, p. 79-95.
Plaza et al. "Medical Personnel and Patient Skill in the Use of Metered Dose Inhalers: A Multicentric Study", Respiration 1998, vol. 65, p. 195-198.
Patton et al. "Inhaled Insulin", Advanced Drug Delivery Reviews 1999, vol. 35, p. 235-247.
Alpar et al. "Biodegradable Mucoadhesive Particulates for Nasal and Pulmonary Antigen and DNA Delivery", Advanced Drug Delivery Reviews 2005, vol. 57, p. 411-430.
Musante et al. "Factors Addecting the Deposition of Inhaled Porous Drug Particles", Journal of Pharmaceutical Sciences Jul. 2002, vol. 91, No. 7, p. 1580-1590.
Groneberg et al. "Fundamentals of Pulmonary Drug Delivery", Respiratory Medicine 2003, vol. 97, p. 382-387.
Frijlink et al. "Trends in the Technology-Driven Development of new Inhalation Devices", Drug Discovery Today: Technologies 2005, vol. 2, No. 1, p. 47-57.
Crompton "How to Achieve good Compliance with Inhaled Asthma Therapy", Respiratory Medicine 2004, vol. 98, p. S35-S40.
Cohn "A Review of the Effects of Medication Delivery Systems on Treatment Adherence in Children with Asthma", Current Therapeutic Research Jan. 2003, vol. 64, No. 1, p. 34-44.
Meadows-Oliver et al. "Asthma Medication Delivery Devices", Journal of Pediatric Health Care 2005, vol. 19, p. 121-123.

* cited by examiner

INHALER

The present invention relates to inhalers, and in particular to inhalers used for the delivery of a drug medicament, such as formulations comprising a dry pharmaceutical powder, a wet pharmaceutical formulation, or a drug solution etc, to a human lung via the nose or mouth of a user.

Different inhalers can be divided into three categories: nebulizers; pressurized metered dose inhalers (pMDI) and dry powder inhalers (DPI). Nebulizers are bulky, not portable, and difficult to set-up, although they can delivery high dose of drugs, and need little effect from a patient to coordinate the dispersion and inhalation, and produce less deposition in the oropharynx comparing to the pMDI. Cross contamination among users using same nebulizer is another problem.

Introduced in 1956, pMDIs are portable, easy and ready to use. They dominated the inhaler market since their appearance until the late 20th century, because of their fatal inherent disadvantages as the essential requirement of a propellant. Chlorofluorocarbons (CFCs) were initially used as a propellant, but they were banned in 2005 because of their effect of depleting the ozone layer. The replacement hydrofluorocarbons (HFCs) do not affect the ozone layer, but their vapour has a much stronger green house effect (2000 times) than carbon dioxide. This datum alone foretells that pMDIs' future is not brilliant due to their contribution to global warming. In addition to this, all pMDIs need the patients to carefully coordinate their inhalations with the dispersion of drugs. They also produce more drug deposition in the mouth and throat of a user and hence cause stronger side effects. Even if the introduction of a breath-actuator and a spacer to the development of pMDI alleviated these problems, 91% of patients were unable to use their pMDI correctly compared with 85% of nurses and 72% of physicians in Europe.

DPIs have an obvious "green" advantage over the pMDIs. In today's market, there are different DPIs available, such as single dose DPIs, reservoir based DPIs, and multiunit-dose DPIs. Reservoir based DPIs meter doses of the drug in the device out of a powder reservoir to provide multi-dose medication. The multiunit-doses DPIs contain multiple pre-measured individually packed doses of drugs. A DPI using auxiliary energy to make aerosolisation independent of the user's inhalation is defined as an active DPI, whereas one using only the user's inhalation to entrain and disperse the drug powder is referred to as a passive DPI.

Examples of prior art passive DPIs, either breath-actuated or not breath-actuated, are given in the following. WO 03/082389 describes a multi-dose dry powder inhaler using a single dose blister strips to deliver a powder medicament. EP 0,069,715 describes a reservoir based multi-dose DPI using perforations in a membrane to deliver a unit dose of drug powder from a powder reservoir to the air conduit where the powder is entrained, dispersed and then inhaled by the user. To assist dispersion, a propeller rotating upon the user's inhalation is also integrated into the mouthpiece.

Similar multi-dose passive DPIs are also disclosed in patents or patent applications U.S. Pat. No. 6,971,384; U.S. Pat. No. 6,769,601; U.S. Pat. No. 6,098,619; U.S. Pat. No. 6,655,381; U.S. Pat. No. 6,273,085; U.S. Pat. No. 6,561,186; U.S. patent application Pub. No. US 2005/0005933 etc. Although these documents disclose various unique points to be patented, their modifications do not change the basic operational mechanism described hereafter.

For these DPIs, the entrainment and the dispersion of the drug powder is rarely perfect because of the input energy being uniquely determined by the user's inhalation, especially for an asthma patient with a breathing difficulty. The design idea of these DPIs is therefore in conflict with itself. On the one hand, they are designed to heal the breath problems for their targeted users, whereas, on the other hand, they want to get the best from the user's worsened inhalation.

U.S. Pat. No. 5,511,540 describes a breath-actuated pMDI using a spring to provide the priming force. The spring must be strong enough to hold the canister or container in the right position, whereas it must exert a force on a trigger, and the force must be light enough for the inhalation of a user to easily actuate the trigger. A subtle balance makes the inhaler less universal. In addition to this, the inhaler operates in such a manner. The user must inhale first and at a predetermined flow rate of the inhalation, a trigger device is actuated and consequently it causes a movement of the container to release the drug. The inhalation airflow rate of 15 to about 60 L/min are sufficient to actuate the trigger. A similar example is given in U.S. Pat. No. 6,260,549 with a low actuation airflow rate. Needless to say, this mechanism itself is in conflict with the basic principle of designing a perfect inhaler. Instead of making the best use of the user's inhalation, to some extent it wastes part of the inhalation itself. This waste may be the most important part of the user's inhalation for an excellent drug delivery to the deep lung.

In U.S. patent application US 2004/0187868, a breath actuated active DPI is disclosed. In this invention, the elastic energy stored in a pressed spring is released to produce compressed air once airflow rate is in a preset range detected by a sensor. The speed of the compressed air is higher than sonic speed. The high-speed air is used to entrain and aerosolise the drug powder. The aerosol then joins the inhaled air and is delivered to the lung. A similar DPI is disclosed in U.S. Pat. No. 6,012,454, another is disclosed in UK patent application GB 2 405 799, whereas U.S. Pat. No. 6,901,929 discloses a manually actuated active DPI.

It is clear that the breath actuated DPIs cannot make the best use of the user's inhalation, as the first part of the user's whole inhalation, which is very important for deep lung delivery, is always used to actuate a trigger or a trigger system so as to release the auxiliary energy. In addition to this, the active DPIs using pressurized air as auxiliary energy have a common problem of drug powder losses onto the surface of the user's mouth and throat due to the high particle speed as a result of the quick release of the pressurized air. For the non-breath actuated inhalers, there is another problem as they just leave the oldest coordination problem to the user. For the breath actuated inhalers, they too waste part of the user's inhalation due to the inherent nature of their breath actuation mechanism.

Thus there is still a need for improving inhalers where the user's inhalation is fully used to deliver a well-dispersed drug powder aerosol to the targeted region in the lung; where the user's entire inhalation can continue to entrain and disperse the drug residue, which is not entrained by the auxiliary energy, and then deliver it to the user's lung; where the coordination between the drug dispersion and the user's inhalation is automatically controlled so that the user can take the medicament with little effort; where the excellent drug dispersion or aerosolisation is achieved by using an auxiliary energy; where the auxiliary energy for dispersing the drug can be breath actuated; where the speed of the aerosolised particles can be to some extent controlled. Such a device should also be simple, robust, universal, user and environmental-friendly.

It is therefore an object of the present invention to obviate or mitigate one or more of the problems of the prior art, whether identified herein or elsewhere, and to provide improved inhalation devices or inhalers that can make the best use of the user's inhalation to deliver an aerosolised drug powder to a targeted area in the lung.

Therefore, according to first aspect of the invention there is provided an inhaler for dispensing medicament, the inhaler comprising auxiliary energy provision means for providing auxiliary energy for aerosolising medicament; energy release means for releasing auxiliary energy from the auxiliary energy provision means; feed means for feeding a dose of aerosolised medicament to a user, characterised in that the inhaler comprises control means for controlling a time interval between aerosolisation of the medicament and the user's inhalation, wherein the inhaler is operable, in use, to aerosolise medicament using the auxiliary energy, and harness the user's inhalation to deliver the aerosolised medicament to the user.

Advantages in the inhaler according to the invention reside in its ability to automatically control the coordination between medicament aerosolisation and the user's inhalation, such that the user only needs to breathe naturally to inhale the medicament. Furthermore, actively aerosolising the medicament from a powder using the auxiliary energy in addition to the traditional passive aerosolisation or dispersion of the medicament with the user's inhalation leads to higher drug delivery efficacy, than relying solely on the inhalation passive energy or solely on the auxiliary energy. Also, advantageously, the user's entire inhalation is used to deliver the aerosolised medicament, and therefore there is no waste of the user's inhalation.

By the term "aerosol", we mean a collection of particles suspended in a gas. The term refers collectively to both the particles and the gas in which the particles are suspended. The particle size may range from about 0.002 μm to more than 100 μm, ie from a gathering of a few medicament molecules to the size where the particles no longer can be carried by the gas.

The skilled technician will appreciate that the terms "drug" and "medicament" are used interchangeably herein, and are non-limiting.

The medicament may be in any formulation prior to aerosolisation. For example, the medicament may be in the form of a dry powder, or a wet formulation, ie a solid suspension in a propellant. Alternatively, the medicament may be in the form of a solution. Preferably, the medicament is in the form of a powder, which is then aerosolised upon action of the auxiliary energy to form the aerosol. The aerosol medicament is then inhaled by the user and delivered to a targeted area of the user's lung. Preferably, the feed means is operable to feed a dose of aerosolised medicament to the user's lung. Hence, it is preferred that the inhaler is a dry powder inhaler. Preferably, the auxiliary energy provision means is operable to provide auxiliary energy for aerosolising medicament powder to form a medicament aerosol. The energy release means may be operable to release the auxiliary energy upon suction or inhalation by the user. This is referred to herein as a "suction-actuated" actuation. Alternatively, the energy release means may be manually operated by the user, for example, to release the auxiliary energy. It is believed that both "suction-actuated" actuation and manual actuation obtain excellent aerosolisation of the medicament.

Preferably, the energy release means is operable in use to release the auxiliary energy either manually, or upon suction, or inhalation, by the user.

Preferably, the control means is operable to control the time interval between the aerosolisation of the medicament and the user's inhalation in such a manner that the user's inhalation only gets through into the user's mouth after aerosolisation has occurred for a certain time period.

Preferably, the feed means is operable to feed a unit dose of medicament and activate the suction-actuation mechanism. It will therefore be appreciated that the feed means preferably serves two functions, namely (i) feeding powder medicament from medicament storage means to site where it is aerosolized; and (ii) feeding aeroslised medicament to the user, and preferably the lung.

Preferably, wherein the auxiliary energy provision means is in operable communication with any combination of the energy release means, the control means, and/or the feed means, and preferably, by a conduit. Preferably, the conduit couples the energy release means with the control means. The conduit may or may not couple the energy release means with the feed means. The conduit may comprise an air channel.

Preferably, the feed means is in operable communication with the control means by a conduit. Preferably, the conduit couples the control means with the energy release means. Preferably, the conduit is an air channel. The conduit may or may not couple the control means with the auxiliary energy provision means.

A significant advantage of the inhaler according to the invention is that two forms of energy are used to aerosolise and deliver the medicament to the user, ie passive energy provided by the user's own inhalation, and auxiliary energy provided by the auxiliary energy provision means. The skilled technician will appreciate that various types of auxiliary energy may be used to supplement the passive energy. For example, the auxiliary energy may be independently selected from a group comprising:—electrical based energy; vibration-based energy; motored propeller based energy; and compressed gas-based energy.

The auxiliary energy provision means may comprise a gas reservoir for containing gas. Preferably, the auxiliary energy provision means comprises means for charging or compressing the gas. The volume of the gas increases from a lower value when it is in a rest or uncharged state (ie uncompressed), to a larger value when it is charged or compressed. The compressed or charged gas provides the auxiliary energy for aerosolising the medicament.

Preferably, the auxiliary energy provision means comprises a container in which charged or compressed gas may be stored. Suitably, the container is made of a material that can stand a relatively high pressure, for containing said compressed or pressurized gas. Preferably, the volume of the container is adapted to vary in response to a change in the pressure of the gas contained therein.

The container preferably comprises at least one cylinder. The container may comprise two substantially parallel cylinders. The container may comprise a plurality of cylinders mounted on a cylinder base that is cylinder shaped or cubic shaped, or takes the shape of other polyhedrons, preferably, having at least one void therein, wherein all of the cylinders may be in operable communication with each other.

Preferably, the container comprises at least one aperture, and preferably, a plurality of apertures, by which it may be coupled or connected with the energy release means, control means and/or the feed means. The apertures may also be used to connect or couple the container with other accessories, such as a check valve, pressure gauge or pump etc.

It is preferred that the effective volume of the gas container is operable to change in response to the change in pressure therein. Preferably, the gas container comprises a piston slideably mounted therein, which piston is moveable between a first, "rest position" in which the volume of the container is at a first low value when the pressure of gas in the container is at a first low value, and a second, "engaged position", in which the volume of the container is at a second higher value when the pressure of gas in the container is at a second higher value.

When the piston is in the first position, the container is divided into two sections, which are denoted volumes V1 and V2. It should be appreciated that only V1 acts as the gas reservoir. When the piston is in the second position, the effective volume of the gas container is V1 plus V2.

Preferably, the container comprises biasing means operable to bias or urge the piston towards the first position. When the pressure of gas in the container increases, the volume of the container increases thereby compressing the biasing means. Upon release of the pressure in the container, the piston is biased towards the first position. Hence, preferably, the biasing means is adapted to urge the piston back to the first position once the gas pressure drops to a certain value after the release of compressed gas from the gas container.

A first end of the biasing means is preferably attached to an inner surface of the container, and a second end of which is attached to the piston, and preferably an open end thereof. The biasing means may comprise a spring, such as a helical spring.

Hence, it will be appreciated that the effective volume of the gas container changes in response to the change in its pressure. Both changes in gas volume and pressure may be easily detected and used to couple the auxiliary energy provision means with the other features of the inhaler.

The means for charging the gas in the container may comprise a manually operated piston pump. The means for charging the gas may comprise a supply of compressed gas, such as oxygen, nitrogen or mixtures thereof, or air. The means for charging the gas may comprise a supply of propellant, such as hydrofluorocarbons.

Preferably, the energy release means is operable in use to rapidly release the auxiliary energy from the energy provision means to the feed means and thereby to aerosolise the medicament. Preferably, the release means comprises a valve adapted to control the air channel between the auxiliary energy provision means and the feed means. The valve is preferably operable to adopt a first "engaged position" in which it is closed, thereby closing the air channel between the auxiliary energy provision means and the feed means, and a second "rest position" in which it is open, thereby opening the air channel between the auxiliary energy provision means and the feed means. The energy release means may further comprise means for opening the valve.

The valve may comprise a mechanical valve, or an electrically-controlled valve. However, preferably, the valve comprises a piston which is slideably mounted within a body and moveable between a first, "engaged position" in which it is closed, thereby closing the air channel between the auxiliary energy provision means and the feed means, and a second "rest position" in which it is open, thereby opening the air channel between the auxiliary energy provision means and the feed means.

The body has an aperture at least adjacent a first end thereof for accommodating a first rod member, and an aperture at least adjacent a second end thereof for operable communication with the feed means, preferably, by the air channel. Preferably, the piston comprises sealing means for sealing the piston in the body but still allowing sliding therealong. The sealing means comprises a rubber ring member. The first rod member may comprise a handle at one end thereof. The body may be a cylinder. Preferably, the valve comprises biasing means for biasing the piston towards the "rest position". Preferably, the biasing means is disposed between the handle on the first rod member and the aperture provided at least adjacent the first end of the body, thereby biasing the piston towards the rest position to thereby open the air channel, when the means for opening the valve is actuated. The biasing means is preferably a spring, and preferably, a helical spring.

Preferably, the body comprises an aperture in its side by which the body may be connected to the auxiliary energy provision means by the air channel. The body may comprise receiving means for accommodating a second rod member attached to one end of the piston. The receiving means may comprise a trough and notch arrangement.

Preferably, when the second rod member is in the "engaged position", the piston is urged towards the engaged position to close the air channel, and the second rod member maintains the piston towards the engaged position.

The means for opening the valve may comprise a trigger, which may be actuated manually, or by a suction force created by a user's inhalation. Hence, in a preferred embodiment, the means for opening the valve may comprise a body comprising an aperture at least adjacent a first end thereof by which the body may be operably connected to, or coupled with, the feed means, preferably by the air path. It is preferred that a second end of the body is open. The body may be a cylinder.

The means for opening the valve may further comprise a piston slideable between a first, "engaged position" in which the valve is closed and a second, "rest position", in which the valve is open.

A first end of the piston may be open and a second end of which is closed. Preferably, the piston comprises sealing means for sealing the piston in the body but still allowing sliding therealong. The sealing means is preferably a rubber ring member.

A first side of the body may comprise an aperture for accommodating a manual release means. A second side of the body may comprise a receiving means for accommodating a first elongate member attached to the piston. The receiving means may be disposed at least adjacent the open end of the body. In use the user may manually move the piston. The body may comprise abutment means for preventing further movement of the piston in the body. The abutment means may be disposed at least adjacent the receiving means. Preferably, the abutment means is adapted to engage a hook by which the piston is maintained in the rest position by hooking the second rod member. The abutment means may be a screw.

The valve preferably comprises a hinge, which is attached at a predetermined position at least adjacent the receiving means, and which is operable to couple with the means for opening the valve.

Preferably, the means for opening the valve further comprises a lever, pivoted to the hinge, and comprising two arms forming an angle of between about 0°-180°, more preferably, between 20°-160°, and even more preferably between about 40°-140°. Preferably, one of the arms comprises a ball. Preferably, the angle formed between the two arms is 70°-120°.

Preferably, in use, a wedge is inserted into the piston from its open end to thereby transmit a position shift of said piston to a vertical shift of one arm of the lever that is put in a position to make the ball contact the wedge and thereby enable the other arm of the lever to open the valve.

Preferably, the means for opening the valve comprises biasing means for biasing the lever towards the rest position. The biasing means may be mounted on the hinge. The biasing means may be a spring.

Preferably, in use, when the user inhales, the suction force drives the piston to move together with the wedge, thereby driving the lever to open the valve. Accordingly, this means that the user's inhalation on actuation is not wasted. Advantageously, the manual release button is easy to use for a user with a weak suction force.

Preferably, in embodiments where the means for opening the valve is a trigger, it may comprise a body having a piston slideably mounted therein, moveable between a first, "engaged position", in which the valve is kept close and a second, "rest position", in which the valve is open.

A rod member may be attached to the piston. Alternatively, the means for opening the valve may comprise a body having a diaphragm extending thereacross to which a rod may be attached. The body may be a cylinder.

Preferably, the control means comprises a valve for controlling air entering the user's mouth via the air channel. The valve may be a mechanical valve or an electrically controlled valve.

Preferably, the valve comprises sensing means for detecting the charge and release of the auxiliary energy. Preferably, the valve comprises control means, and a timer. Preferably, the means for controlling the valve may only be actuated to open the valve after the sensing means has detected the release of auxiliary energy for a pre-determined time period controlled by the timer.

Advantageously, such working procedures guarantee aerosolisation of the medicament always happens in advance of the user's inhalation and furthermore, that substantially all of the user's inhalation is used to deliver aerosolised medicament to the user's lung.

The valve may comprise a body comprising an aperture at least adjacent a first end thereof by which the body is maintained at atmospheric pressure. The body preferably comprises an aperture at least adjacent a second end thereof, and preferably a further aperture for operable communication of the body with the air channel. The further aperture may be provided in the side of the body.

The valve preferably comprises a piston slideably mounted in the body moveable between a first, "rest position" in which the valve is open to connect the air channel with the atmosphere and a second, "engaged position", in which the valve is closed, thereby preventing air entering the air channel. It will be appreciated that this would otherwise equalise the air pressure therein.

Preferably, the valve comprises sealing means for sealing the piston in the body but enabling sliding to occur. Furthermore, the sealing means separates the apertures in the body so the body acts as a valve. The sealing means may comprise a rubber ring mounted to the side of the piston.

The valve preferably comprises a rod member attached to the piston via the aperture at the second end thereof. The rod member preferably comprises a handle. The valve preferably comprises biasing means adapted to bias the piston towards a rest position from an engaged position. The biasing means is preferably mounted between the handle and the aperture in the second end of the body.

The sensing means for detecting the charge and release of auxiliary energy is preferably adapted to detect a change in volume or pressure of the gas reservoir or the position of the piston therein. For example, the sensing means may comprise a piston adapted to directly detect and react to the changes in both volume and pressure of the gas reservoir. Such a reaction may include a movement corresponding to the change in volume/pressure of the gas reservoir. Alternatively, the sensing means may comprise a pressure gauge that can detect the change in pressure of the reservoir. Advantageously, the use of the piston as a sensor and as a reactor, ie. in response to the signal it senses, helps to simplify the inhaler making it more compact as seen in the Figures.

In embodiments where the means for controlling the valve is a trigger, it may be selected from a group comprising a rod member; a mechanical trigger; and an electrical controlled trigger.

Preferably, the trigger comprises a body comprising an aperture at least adjacent a first end thereof, and an aperture at least adjacent a second end thereof, and a piston slidably mounted therein. The trigger may comprise a rod member a first end of which is attached to the piston by the aperture at the second end of the body, and a second end of the rod member is attached to the handle.

In one particularly preferable embodiment, the timer may be an inherent timer, formed by a combination of the auxiliary energy provision means and the control means, and wherein the pre-determined time period is a cooperative result of this combination.

Alternatively, the timer may be a combination of the inherent timer and an external timer coupled with the rod member. Hence, preferably, the coupled rod member is only able to return to a rest position from an engaged position after the external timer has been actuated for a preset time period.

The feed means is preferably adapted to feed powder medicament from medicament storage means to the cavity where it is aerosolized; and also feed aeroslised medicament to the user, and preferably the lung. The feed means is adapted to feed a unit medicament dose of the medicament and preferably, activate the suction-actuation mechanism.

Preferably, the feed means comprises a mouthpiece. Preferably, the feed means comprises a body, which comprises a plurality of apertures for connecting the mouthpiece and the energy release means and the control means, and optionally, a plurality of cavities for storing and feeding medicament. The body may comprise two pieces, which are fused together, and having sealing means therebetween. The sealing means, for example, a rubber seal, may be disposed within a trough in each body piece. Advantageously, the sealing means protects the medicament from moisture in the atmosphere.

Preferably, the feed means further comprises means for entraining and dispersing the medicament. The means for aerosolising medicament may comprise a gas conduit through which gas may flow to thereby entrain and aerosolise the medicament. The conduit is preferably spiral shaped for generating a substantially spiral or vortexed flow of gas therein.

Alternatively, the means for aerosolising the medicament may comprise means for introducing gas into a cavity at an angle such that medicament exits the cavity in a substantially perpendicular direction so as to produce cyclone flow of the gas therein, and thereby entrain and aerosolise the medicament.

The feed means for feeding a dose of medicament and activating the suction-actuation mechanism may comprise a dose counter, and an external timer.

The feed means may comprise a body in which a piston is slideably mounted, which slideable between a first, "rest position" in which the medicament is loaded and a second, "engaged position", in which the medicament is fed to the cavity. The body may comprise an aperture at least adjacent a first end thereof for connection with the auxiliary energy provision means and an aperture at least adjacent a second end thereof. The piston may comprise sealing means for enabling sliding within the body.

Preferably, the feed means comprises a slide or a rod having an aperture by which it may be attached to, or coupled with, the piston by the aperture at the second end of the body. Preferably, a first end of the slide or rod is received by receiving means disposed between two body pieces of the drug feeder. Preferably, a second end of the slide or rod is coupled with the dose counter and an external timer.

Preferably, the feed means comprises biasing means for biasing the slide after it has been released by the external timer. The biasing means is preferably disposed between the aperture at the first end of the body, and the two body pieces.

Preferably, one of the two apertures in the slide is operable to feed medicament, and the other aperture is operable to open the air path for the suction-actuation mechanism so that the user can only inhale after the inhaler has properly fed medicament.

The inventor believes that the use of the sensing means in the inhaler according to the first aspect for detecting changes in the gas reservoir is an important feature of the invention.

Hence, in a second aspect, there is provided an inhaler for dispensing medicament, the inhaler comprising a gas container for containing compressed gas; sensing means operable to either detect, directly or indirectly, a change in the volume and/or the pressure of the gas in the reservoir, and means for aerosolising the medicament in response to a signal detected by the sensing means, wherein the inhaler is operable, in use, to aerosolise the medicament using the compressed gas, and harness the user's inhalation to deliver the aerosolised medicament to the user.

The volume of the gas container increases from a lower value when it is in a rest or uncharged state, to a larger value when it is charged or compressed.

The compressed or charged gas provides an auxiliary energy in addition to the energy provided by the user's inhalation, for aerosolising the medicament.

Preferably, the inhaler of the second aspect comprises means for controlling the time interval between medicament aerosolisation and the user's inhalation in response to the signal detected by the sensing means.

The medicament may be in any formulation prior to aerosolisation. It is preferred however that the inhaler is a dry powder inhaler.

Preferably, the gas container is operable to provide auxiliary energy for aerosolising medicament powder to form a medicament aerosol. The inhaler may comprise energy release means operable to release the auxiliary energy either manually or upon suction or inhalation by the user.

The gas container may be defined as being auxiliary energy provision means because it contains gas, which may be pressurised (ie compressed) to thereby generate auxiliary energy with which the medicament is aerosolised. The volume of the gas increases in the container from a lower value when the gas is in a rest or uncharged state, to a larger value when the gas is charged or compressed. The compressed or charged gas provides the auxiliary energy for aerosolising the medicament.

Preferably, the volume of the gas container is adapted to vary in response to a change in the pressure of the gas contained therein.

It will be appreciated that many features of the inhaler of the second aspect are identical to those as defined in relation to the inhaler of the first aspect. Surprisingly, the inhaler according the first and second aspects is very effective in methods for administering medicament to a patient.

Hence, in a third aspect, there is provided a method of administering a dose of medicament to a subject, the method comprising the use of an inhaler according to either the first or second aspect.

In accordance with the invention, exemplary systems, apparatus and methods for aerosolising and delivering a powdered medicament to a human lung are given. The above and other objects of the invention are realized to specific embodiments of an exemplary inhaler having a mouthpiece; a drug feeder with a drug powder reservoir; a valve that is called the primary valve, valve one or valve A used to control the release of an auxiliary energy for dispersing the drug powder; a trigger that is called primary trigger, trigger one or trigger A used to control the first valve; a compressed gas reservoir or simply named as gas reservoir of which the volume changes with the change in its pressure; a sensor or sensors that detect the changes in either volume, or pressure or both of the gas reservoir; second valve that is named secondary valve, valve two or valve B used to control the intake of fresh air from the outside environment by a user; second trigger that is called secondary trigger, trigger two or trigger B used to control the second valve; a timer that is called primary timer, timer one or timer A; a dose counter; second timer that is named as secondary timer, timer two or timer B; an air channel, part of which is also used to disperse and deliver the drug powder; an air path that is used to actuate trigger one.

In one particular aspect, the mouthpiece is made of plastic. It is shaped on one side in such a way that a user can comfortably put into his/her mouth and airtight it with his/her lips. On the other side it is shaped in a manner matching with one side of the drug feeder. Inside it, there is a conical hollow hole. The side with a small hollow area is attached to one side of the drug feeder coaxially with the air channel. Such a structure is advantageous in that the speeds of the aerosolised particles can be reduced before being inhaled into the user's mouth.

In one particular aspect, a spacer is inserted between the mouthpiece and the drug feeder. This structure is advantageous in that the aerosols get more time to slow down and also more time to evaporate in case of a liquid propellant being used.

In one particularly preferable aspect, the drug feeder has a body made of two plastic pieces, a drug-feeding slide and two rubber sealing gadgets. Inside the body there are a drug powder reservoir, a cylindrical cavity for feeding and dispersing the drug, and an air channel that is separated into two parts by the cavity, an air path and an integrated dose counter. There are troughs at the interface of these two pieces so as to accommodate rubber sealing gadgets and the slide.

In one particularly preferable aspect the slide in the drug feeder is made of light metal or alloy or other material that are electric conductive and compatible with the drug stored in the powder reservoir. It has two holes. The slide can move along a trough between two positions. When the slide is in a recess position or a loading position, one hole named drug-feeding hole is coaxially located within the powder reservoir. The other one named air path valve blocks the air path. When the slide is pushed into a forward position or a feeding position, the drug-feeding hole with fixed volume of drug is located in the cavity and is coaxial with the air channel connecting the mouthpiece. The other hole is aligned with the air path and becomes part of the air path. The dose counter is coupled with the slide in such a manner that it only reacts with one of the two movements of the slide, either forward or recess so as to increase only one number after one dose of drug is fed and consumed. This configuration is advantageous in that simply coupling the movement of the slide with drug feeding, dose counter actuation and the trigger are interlocked.

This simple structure also makes the drug delivery consistent. The diameter of the feeding hole and the thickness of the slide determine the volume of drug powder being fed. Both of them can change to suit different requirements of different drug powders. The change in diameter of the feeding-hole is easy. By changing the slide with different diameter of the drug-feeding hole, the inhaler is therefore adaptive and universal. Although a slide is preferably used for feeding the drug, other shaped material such as a round rod, a ball or an oval rod etc. can also be used for the same purpose.

In one particularly preferable aspect of the invention, the slide is connected with a piston at one end and the timer one at the other. When the slide is driven to a forward position, timer one is engaged with the slide. The slide is then released after a preset time period and freely moves back. The piston can move freely in a cylinder. It moves forward as a reaction to a signal from the sensor. A spring is used to bias it back to a rest position. This configuration is very user-friendly. In combination with the breath actuated trigger one, what the user only needs to do is to close the valve one, fill the gas reservoir to a preset pressure and then just inhale. This configuration guarantees that the intake of a medicament by the user happens only when the drug is properly fed, the gas reservoir is properly charged.

A timer is preferably used to control the time period between the actuation of timer one and the release of the slide from the feeding position. However other means can also be used to achieve the same function. For example in the simplest case, a latch and just a latch can be used to keep the slide in the feeding position for desired time period. Then manually moving the latch to other position releases the slide.

In one particular aspect, special shaped rubber gadgets are used to prevent the drug powder reservoir from the invasion of moister from the air channel, air path and the outside environment. The gadgets are designed to seal properly whereas the slide can still move freely between two positions.

In one particular aspect, the two parts of the air channel in the two pieces of the drug feeder are coaxially with the cylindrical cavity. In another embodiment, the one in connection with the mouthpiece is coaxial with the cylindrical cavity whereas the other one enters the cavity at an optimised angle.

In one particularly preferable aspect, trigger one is breath actuated. It comprises a piston, a cylinder, a lever and a wedge etc. There is a hole on a circular end of the cylinder to connect the air path whereas the other circular end of the cylinder is open. The lever is pivoted onto a hinge attached to the surface of valve one. A spring mounted on the hinge is used to bias it to a rest position. The piston is hollow and sealed at one circular end. The other circular end of the piston is open so as to accommodate the wedge, which is shaped to be able to integrate into the cavity of the piston to create a slope. One end of the lever is in touch with the surface of the slope. At rest position, there is a free space between the end of the cylinder connected with the air path and the piston. When the user sucks from the mouthpiece, the only air being inhaled is the air contained in this closed control system. So there is no inhalation wasted for such a breath-actuated trigger, more precisely suction actuated trigger. The suction forces the piston to move towards the end of the cylinder. The slope moving along with the piston forces the lever downwards. The other side of the lever then moves correspondingly to open valve one. The advantage of this configuration is no waste of the user's inhalation for breath actuating the release of the auxiliary energy, needless to say it is user's friendly and easy to use.

Although a piston with a wedge is used to move the lever, it is not exclusive. Other means such as a rod attached to a piston or a diaphragm etc. can also be used for the same purpose.

In one particularly preferable aspect, a button is attached to the cylinder of trigger one. It is used to manually turn valve one on in case that the user is too weak to suction actuate trigger one. In a given simplest example, it comprises a long bolt with a stud on one end, a nut and a spring. The spring is used to bias it to a rest position while the nut is used to prevent it flying away from the cylinder. It is positioned at some point over the lever so that when it is pushed down, the lever is pushed down too. This simple configuration has obvious advantages for users whose inhalations are so weak as not be able to actuate trigger one.

In one particular aspect, trigger one also has a hook pivoted on a screw attached on one side of the cylinder, a round rod attached on the surface of the piston and a trough on the cylinder. The hook in combination with the rod is used to hold the piston in the rest position so as to keep the piston stable while the inhaler is not in use. The user can also use this function to check the inhaler without actuating both triggers.

In one particular aspect, valve one comprises of a cylinder, rubber ring sealing gadgets, a piston with an attached rod having a handle bar and a spring. The rubber ring gadgets mount onto grooves carved at proper positions of the side of the piston. On one side of the cylinder, a hole, or hole one, connects the gas reservoir via an air channel. On one circular end of the cylinder, another hole, or hole two, connects with the drug feeder via another part of the air channel. On the other circular end of the cylinder is a big opening to accommodate the rod. The cylinder also has a trough on one side. There is a notch at one end of the trough. The notch is used to hold the short rod attached on one circular end of the piston when the user manually engages the piston to close valve one. The spring sandwiched between the handle bar and the opening of the cylinder is pressed when the piston is in the engaged position. Upon the movement of the pivoted trigger lever, the short rod leaves the notch and the piston is biased back to the rest position. The valve one is then opened to allow the compressed gas goes through. The compressed gas goes into the closed cavity of the piston and helps the spring bias the piston back to rest position. Such a configuration has an advantage of rapid opening valve one, and hence rapid release of the compressed gas is achieved. A well-dispersed drug powder is expected.

In one particularly preferable aspect, the gas reservoir comprises of a cylinder, a piston, a spring and some accessories such as a release button or a check valve, a pressure gauge, ring sealing gadgets and a piston style pump along with a single direction check valve. The cylinder is particularly preferably made of steel or alloy or engineering plastic that is strong enough to stand high pressure. On one circular end of the cylinder, there are three holes correspondingly connecting with the air channel, a pressure gauge and the pump. One more hole at the same end is used to accommodate the release button. On the other end of the cylinder, it has one hole in connection with trigger two in one embodiment or with trigger two and a cylinder of the drug feeder in another embodiment via air tubes. The piston is movable in the cylinder. When the piston is at rest position, it divides the cylinder into two voids with volume V1 and V2 where the V1 is the effective volume of the gas reservoir at rest state. When air is pumped in, the piston moves from the rest position to the end of the cylinder. In this way the gas reservoir now has a total volume of V1+V2. The gas pressure in the reservoir will increase upon more air being pumped in. Such a configuration guarantees the inhalers being robust and versatile, as the adjustable range of the pressure in the air reservoir is very wide as a result of the strength of the cylinder.

In one particularly preferable aspect, the V2 is bigger than a certain value that is determined by the free volumes of three different parts. The first one V3 is the free space of a cylinder of trigger two when it is at engaged position as described below. The second one V4 is the free volume of the cylinder of the drug feeder when its piston is at engaged position. The third part V5 is the free volume of the tubes connecting the air reservoir with trigger two and the cylinder of the drug feeder. When the gas reservoir is filled with pressurized air, V2 is compressed into a closed space having a smaller volume. A pressure higher than the atmosphere is then created in this space according to Boyle's law: $P1V2=P2(V3+V4+V5)$ where P1 is atmosphere pressure, P2 is the pressure in these closed space. P2 is bigger than P1. The positive pressure therefore drives the related pistons to move from a rest position to an engaged state. Such a configuration automatically couples the movement of the pistons in the gas reservoir, in the drug feeder and in trigger two. While the gas reservoir is being charged with compressed gas, trigger two is automatically driven to an engaged position to close valve two; and the slide in the drug feeder is automatically pushed forward from a loading position to a feeding position. Timer one, timer two in case of being used, the dose counter and the air path all change correspondingly. The configuration is very user friendly and makes the inhaler very reliable and easy to use.

In one particular preferable aspect, the sensor is simply the piston in the cylinder of the gas reservoir. However an electrical sensor or electrical sensors or mechanical gauges can also be used to detect the change in pressure of the gas reservoir. Sensors that can directly or indirectly detect the change in volume of the gas reservoir or the change in the piston position can also be used for the same purpose.

In one particular aspect, trigger two comprises of a cylinder, a piston with a handle and a spring etc. On one circular end of the cylinder, it connects with the air reservoir and the other end is open with a piston stopper. The handle is attached to the piston at one end. At other end it is attached to another piston that is able to slide in the cylindrical valve two. Upon increase in gas pressure of the gas reservoir, the piston is pushed forward along with the handle that in turn closes valve two. The spring sandwiched between the handle and the cylinder of valve two is pressed. When the compressed gas is released, the spring biases the piston backward. The handle goes back along with the piston and hence opens valve two to allow fresh air to get through and go into the user's mouth via the air channel and the mouthpiece.

In one particular aspect, valve two is just a cylinder with two holes on different positions. One at a circular end of the cylinder connects to the atmosphere and the other on a predesigned position of one side connects the air channel. When trigger two is in engaged state, the two holes are separated by rubber sealing rings mounted on the side of the piston. Such a configuration guarantees that no air is inhaled before the compressed gas is released to disperse the drug powder. In combination with timer two, inhalers with such a configuration thoroughly sorts out the oldest coordination problem. It is therefore user friendly and easy to use.

In one particularly preferable aspect, timer two is just the combination of the gas reservoir, trigger two and valve two. In this case timer two is called an inherent timer. The total time interval T between the dispersion of the drug powder and the user's inhalation consists of two different parts. The first part T1 is the release of the compressed gas in the air reservoir to a fixed pressure. T1 is determined by the pressure in the gas reservoir and the biasing force of the spring in trigger two. The second part T2 is the time needed for trigger two to move from a close position to an open position. T2 is decided by the biasing force of the spring of valve two, the movement of the piston in valve two and the distance between two holes of valve two.

Increasing the pressure of the air reservoir will certainly increase the time interval. Normally increasing pressure will increase the interval and therefore reduce the speed of the aerosolised particles more as needed. It is obvious that for a given powder, the higher the air pressure is, the faster the aerosolised particles will fly and the more the time needed to slow them down. Inhalers with such a configuration offer a perfect solution to the question.

In one particular aspect, an external timer two either a mechanical one or an electrical one can be inserted between trigger two and valve two. The external timer two is engaged with the rod in trigger two when the piston is pushed forward. A preset time T3 (normally longer than T1) is set up. Once the pressure in the gas reservoir drops, the pressure in the cylinder of trigger two drops too. This signal in turn actuates the external timer two. The external timer two then releases the rod of the piston after a period of T3 elapses. In this case the total interval T is equal to the sum of T2, T3 and T4 that is the time needed for the pressure in the gas reservoir drops from a charged value to the preset one actuating the external timer two.

It is apparent for a skilled in the art that a notch-key method can be easily used for engaging the external timer two and the rod. An integrated pressure sensor in the gas reservoir will be easily adapted to actuate the external timer two.

In a further aspect, there is provided an inhaler for dispersing a drug powder to form an aerosol and delivering said aerosol into a targeted area of a user's lung comprising:

(a) first device for providing an auxiliary energy for dispersing said drug powder to form an aerosol;
(b) second device for quick releasing of said auxiliary energy in either a suction-actuated manner or a manually releasing way so as to obtain a good aerosolisation of said drug powder;
(c) third device for controlling the time interval between said aerosolisation of said drug powder and the user's inhalation in such a manner that the user's inhalation only gets through into the user's mouth after said aerosolisation happens for a certain time period;
(d) fourth device for feeding a unit drug dose of said drug powder and activating said suction-actuation mechanism;
(e) said first device connecting with said second device via a air channel and coupling with said third device and said fourth device;
(f) said fourth device connecting with said third device via a air channel, with said second device via a air channel and a air path and coupling with the first device;

whereby said inhaler actively disperses said drug powder to form an aerosol using said auxiliary energy and uses all the user's inhalation to deliver said aerosol of said drug powder to a targeted area of the user's lung.

Preferably, said auxiliary energy is selected from the group comprising an electrical based energy as a electrical vibrator or a motored propeller etc and a compressed gas based energy.

Preferably, said first device is a gas reservoir, of which the effective volume changes from one value at rest state to a bigger one when charged, for providing said auxiliary energy in form of compressed gases comprising:

(a) a gas container, made of steel or hard plastics that can stand a relative high pressure, for containing said compressed or pressurized gases;
(b) means for charging said compresses gas into said container.

Preferably, said container includes:

(a) a cylinder used to contain compressed gas, having a plurality of holes on its ends so as to couple or to connect with other said devices or accessories such as a check valve, a pressure gauge and a pump etc;
(b) a piston that can slide in said cylinder;
(c) a spring;

(d) one end of said spring being mounted to a inside surface of a circular end A of said cylinder and the other end of said spring being attached to an opening circular end of said piston that can slide inside said cylinder in response to a change in gas pressure in said gas reservoir;

(e) at rest state said piston being kept stable by said spring in a proper position in said cylinder and therefore dividing said cylinder into two parts of volume V1 and V2, only one of which V1 acts as said gas reservoir, whereas at engaged state said piston being pushed to one end of said cylinder and therefore the effective volume of said gas reservoir turns to be V1 plus V2;

(f) said spring biasing said piston back once said gas pressure drops to a certain value after the release of said compressed gas in said gas reservoir;

whereby the effective volume of said gas reservoir changes in response to the change in pressure; both changes in volume and pressure can easily be detected and used to couple with other said devices.

Preferably, said container can also be chosen form the group comprising:

(a) a pair of parallel cylinder; and (b) a plurality of cylinders mounted on a cylinder base shaped in cylindrical, cubic or other polyhedrons having voids in its centre so that all the cylinders can communicate with each other and having holes on its surface or surfaces so as to connect with accessories or to couple with other said devices; and (c) other containers whose volume can change in response to the change in their inside gas pressure.

Preferably, said means for charging said compressed gas into said container can be selected from the group comprising:

(a) a manually operated piston style pump; and (b) a canister of compressed gas such as oxygen, nitrogen or their mixtures or air; and (c) a canister of propellant such as hydro fluorocarbons.

Preferably, said second device for quick releasing said auxiliary energy comprises:

(a) a valve, used to control said air channel between said first device and said fourth device, selected from the group comprising of a mechanical valve and an electrically controlled valve and a specially designed valve;

(b) means for opening said valve.

Preferably, said specially designed valve comprises:

(a) a piston having rubber ring gadgets mounted on its side, a long rod with a handle bar and a short rod attached to one end whereas the other end is closed;

(b) a spring used to bias said piston to a rest state;

(c) a cylinder having a big opening on its one circular end to accommodate said long rod and a hole on the other end to connect with said fourth device via said air channel;

(d) said cylinder having a hole on one side to connect said first device via said air channel, a trough and a notch at one end of said trough on the other side to accommodate said short rod attached to one circular end of said piston so that when said short rod is pushed to an engaged position, said piston moves to a position to shut said air channel; said short rod keeps said piston in said engaged position;

(e) said spring being sandwiched between said handle and said big opening of said cylinder so as to bias said piston back to rest state from an engaged one to open said air channel when said trigger is actuated;

(f) a hinge, which is attached at a predetermined position just adjacent to said trough, used to couple with said means of opening said valve.

Preferably, said means for opening said valve is a trigger, which can be actuated manually or by a suction force of a user's inhalation and includes:

(a) a cylinder having one hole on one of its circular end to connect with said fourth device via said air path and its another circular end is open;

(b) a piston, having one circular end open and the other circular end close, with mounted rubber ring gadget on its side;

(c) said cylinder has a hole on one side to accommodate a manually release button, a trough on other side so as to accommodate a short rod attached on one side of said piston so that the user can manually move said piston, a screw located at a end of said trough near said open end of said cylinder used to stop the further movement of said piston and to pivotably mount a hook used to hold said piston steady at rest state by hooking said short rod;

(d) a lever, pivoted to said hinge, having two arms having a preferable angle from 70-120 degree, and at the top of one said arm is a ball;

(e) a circular wedge inserted into said piston from its open end so as to transmit a position shift of said piston to a vertical shift of one arm of said lever that is put in a position to make said ball just touch the surface of said wedge and therefore the other arm of said lever move to open engaged said valve;

(f) a spring mounted on said hinge used to bias said lever to a rest state.

whereby when the user inhales, the suction force drive said piston to move and said wedge moves along with it and drives said lever to open said valve so as not to waste the user's inhalation on actuation; whereas the manual release button is an easy choice for a user with weak suction force.

Preferably, said means for opening said valve is a trigger and can be selected from the group comprising:

(a) a cylinder with a piston having an attached rod; and (b) a cylinder with a diaphragm having a attached rod.

Preferably, said third device comprises:

(a) a valve used to control fresh air going into the user's mouth via said air channel; selected from the group comprising of a mechanical valve and an electrically controlled valve and a specially designed valve;

(b) sensors for detecting the charge and release of said auxiliary energy;

(c) means for controlling said valve;

(d) a timer;

(e) said means for controlling said valve can only be actuated to open said valve after said sensors detect the release of said auxiliary energy for a predetermined time period controlled by said timer;

whereby such working procedures guarantee said aerosolisation of said drug powder always happens in advance of the user's inhalation and all the user's inhalation is used to deliver said drug aerosol to a targeted area in the user's lung.

Preferably, said specially designed valve comprises:

(a) a cylinder with one hole at one of its circular end to connect with atmosphere, a big opening at the other circular end, a hole on its side in connection with said air channel;

(b) a piston, sliding in said cylinder, having rubber ring gadgets mounted on its side and used to separate said holes so as to make said cylinder act as a valve;

(c) a rod with a handle attached to said cylinder via said big opening;

(d) a spring mounted between said handle and said big opening and used to bias said piston to a rest state from an engaged one.

Preferably, said sensor or sensors for detecting the charge and release of said auxiliary energy can be selected from a group comprising:

(a) a piston that can directly detect and react to the changes in both volume and pressure of said gas reservoir;
(b) a pressure gauge that can detect the change in pressure of said gas reservoir;
(c) other sensors that can detect the change in pressure of the said gas reservoir and/or the change of the position of said piston;

whereby the use of said piston as a sensor and a reactor, ie in response to the signal it senses, can simplify said inhaler and make said inhaler more compact as seen in the drawings and in the specifications.

Preferably, said means for controlling said valve is a trigger and can be selected from the group comprising:

(a) a rod;
(b) a normal mechanical trigger; and
(c) an electrical controlled trigger; and
(d) a specially designed trigger.

Preferably, said specially designed trigger comprises:

(a) a cylinder having one hole at its one circular end in connection with said first device and a big opening at the other circular end;
(b) a piston with mounted rubber ring gadget, sliding freely in said piston;
(c) a rod attached to said piston via said big opening of said cylinder at its one end and the other end mounted to said handle.

Preferably, said timer is an inherent timer that is a combination of said first device and said third device and said predetermined time period is a cooperative result of said combination. Preferably, said timer is a combination of said inherent timer and an external timer that is coupled with said rod and works in such a manner that said coupled rod is only allowed to move back to a rest state from an engaged one after said external timer being actuated for a preset time period.

Preferably, said fourth device for feeding a unit drug dose of said drug powder and activating said suction-actuation mechanism is called a drug feeder and comprises:

(a) a mouthpiece;
(b) means for entraining and dispersing said drug powder;
(c) means for feeding a unit drug dose of said drug powder and activating said suction-actuation mechanism;
(d) two body pieces airtight sticking together with troughs on their interface so as to accommodate rubber seal gadgets and said means for feeding drug, holes and channels in or through their bodies so as to connect with said mouthpiece and said second device and third device, cavities for storing and feeding said drug powder;

whereby said ring seal gadgets prevent said drug powder from moisture of the outside environment.

Preferably, said means for dispersing said drug powder is selected from the group comprising:

(a) a spiral gas conduit used to make spiral flow of said gas and therefore to entrain and to disperse said drug powder effectively;
(b) said gas being at an optimised angle introduced into a cylindrical cavity where said drug is and exiting said cavity in a perpendicular direction so as to produce cyclone flow of said gas and hence to entrain and disperse said drug powder effectively.

Preferably, said means for feeding a unit drug dose of said drug powder and activating said suction-actuation mechanism comprises:

(a) a dose counter;
(b) a external timer;
(c) a cylinder with a hole on one circular end in connection with said device one and a big opening at the other circular end;
(d) a piston having a rubber ring gadget mounted on its side and sliding in said cylinder;
(e) a slide or a rod having two holes at pre-designed positions and at one end being attached to or coupled with said piston via said big opening of said cylinder, being inserted into a trough between said two body pieces of said drug feeder with the other end being coupled with said dose counter and said external timer;
(f) a spring being sandwiched between said big opening and said two body pieces, used to bias back said feeding slide after being released by said external timer;

whereby one of said two holes is designed to feed said drug powder and the other is designed to open said air path for said suction-actuation mechanism so that the user can only inhale after said inhaler properly feeds said drug powder.

In a still further aspect, there is provided a dry powder inhaler for producing a drug powder aerosol and delivering the aerosolised drug powder to a targeted area of a user's lung comprising:

(a) a gas reservoir used to contain a compressed or pressurized gas, whose effective volume changes from a small value to a big one in response to the increase in the gas pressure and vice versa;
(b) means for charging said gas reservoir;
(c) means for quick releasing said compressed gas in said gas reservoir;
(d) a sensor or sensors that detect the changes of said gas reservoir in volume, in pressure or in both directly or indirectly;
(e) devices that are attached to or coupled with said sensor or said sensors and react to a signal or signals detected by said sensor or said sensors;

whereby said inhaler uses said compressed gas to actively disperse said drug powder to form an aerosol.

Preferably, said means for charging said compressed gas into said container can be selected from the group comprising:

(a) a manually operated piston style pump; and
(b) a canister of compressed gas such as oxygen, nitrogen or their mixtures or air; and
(c) a canister of propellant such as hydro fluorocarbons (HFCs).

Preferably, said gas reservoir for containing said compressed gas can be selected from the group comprising:

(a) a cylinder; and
(b) a pair of parallel cylinder; and
(c) a plurality of cylinder mounted on a cylinder base; and
(d) other shaped containers whose effective volume for containing said compressed gas changes with the gas pressure.

Preferably, said cylinder base has a shape selected from a group comprising a cylindrical shape and a cubic shape or other shaped polyhedron, having a void in the centre, which is used as said compressed gas reservoir and means for connecting all coupled devices, a plurality of holes on a surface or surfaces that are used to connect or communicate with other said devices and some accessories such as a pressure gauge, a check valve, a piston pump etc.

Preferably, said means for quick releasing said compressed gas in said gas reservoir comprises:

(a) a valve, used to control said air channel between said first device and said fourth device, selected from the group comprising of a mechanical valve and an electrically controlled valve and a specially designed valve;

(b) means for opening said valve.

Preferably, said specially designed valve comprises:

(a) a piston having rubber ring gadgets mounted on its side, a long rod with a handle bar and a short rod attached to one end whereas the other end is closed;

(b) a spring used to bias said piston to a rest state;

(c) a cylinder end having a big opening on its one circular to accommodate said long rod and a hole on the other end to connect with one of said devices device via said air path;

(d) said cylinder having a hole on one side to connect said first device via said air channel, a trough and a notch at one end of said trough on the other side to accommodate said short rod attached to one circular end of said piston so that when said short rod is pushed to an engaged position, said piston moves to a position to shut said air channel; said short rod keeps said piston in said engaged position;

(e) said spring being mounted between said handle and said big opening of said cylinder so as to bias said piston back to rest state from an engaged one when said trigger is actuated;

(f) a hinge, which is attached at a predetermined position just adjacent to said trough, used to connect with said means of opening said valve.

Preferably, said means for opening said valve is a trigger, which can be actuated manually or by a suction force of a users inhalation and includes:

(a) a cylinder having one hole on one of its circular end to connect with one of said devices via said air path and its another circular end is open;

(b) a piston, having one circular end open and the other circular end close, with rubber ring gadget mounted on its side;

(c) said cylinder has a hole on one side to accommodate a manually release button, a trough on other side so as to accommodate a short rod attached on one side of said piston so that the user can manually move said piston, a screw located at a end of said trough near said open end of said cylinder used to stop the further movement of said piston and to pivotably mount a hook used to hold said piston steady at rest state by hooking said short rod;

(d) a lever, pivoted to said hinge, having two arms having a preferable angle from 70-120 degree, and at the top of one said arm is a ball;

(e) a circular wedge inserted into said piston from its open end so as to transmit a position shift of said piston to a vertical shift of one arm of said lever that is put in a position to make said ball just touch the surface of said wedge and therefore the other arm of said lever move to open engaged said valve;

(f) a spring mounted on said hinge used to bias said lever to a rest state, whereby when the user inhales, the suction force drive the piston to move and said wedge moves along with it and drives the lever to open said valve so as not to waste the user's inhalation on actuation; for a user with weak suction force, the manual release button is an easy choice.

Preferably, said means for opening said valve is a trigger and can be selected from the group comprising:

(a) a cylinder with a piston having an attached rod; and (b) a cylinder with a diaphragm having a attached rod.

Preferably, said devices that are attached to or coupled with said sensor or said sensors and react to a signal or signals detected by said sensor or said sensors comprising:

(a) first device for controlling the time interval between said aerosolisation of said drug powder and the user's inhalation in such a manner that the user's inhalation only gets through into the user's mouth after said aerosolisation happens for a certain time period;

(b) second device for feeding a unit drug dose of said drug powder and activating said suction-actuation mechanism;

whereby said dry powder inhaler uses said compressed gas to actively disperse said drug powder to form an aerosol first and thereafter uses the user's whole inhalation to deliver said aerosol to a targeted area in the user's lung.

Preferably, said first device comprising:

(a) a valve used to control fresh air going into the user's mouth via said air channel; selected from the group comprising of a mechanical valve and an electrically controlled valve and a specially designed valve;

(b) means for controlling said valve;

(c) a timer;

(d) said means for controlling said valve can only be actuated to open said valve after said sensors detect the release of said compressed gas in said gas reservoir for a predetermined time period controlled by said timer;

whereby such working procedures guarantee said aerosolisation of said drug powder always happens in advance of the user's inhalation and all the user's inhalation is used to deliver said drug aerosol.

Preferably, said specially designed valve comprises:

(a) a cylinder with one hole at one of its circular end to connect with atmosphere, a big opening at the other circular end, a hole on its side in connection with said air channel;

(b) a piston, sliding in said cylinder, having rubber ring gadgets mounted on its side and used to separate said holes so as to make said cylinder act as a valve;

(c) a rod with a handle attached to said cylinder via said big opening;

(d) a spring mounted between said handle and said big opening and used to bias said piston to a rest state from an engaged one.

Preferably, said means for controlling said valve is a trigger and can be selected from the group comprising:

(a) a rod;

(b) a normal mechanical trigger; and (c) an electrical controlled trigger; and (d) a specially designed trigger.

Preferably, said specially designed trigger comprises:

(a) a cylinder having one hole at its one circular end in connection with said first device and a big opening at the other circular end;

(b) a piston with mounted rubber ring gadget, sliding freely in said piston;

(c) a rod attached to said piston via said big opening of said cylinder at its one end and the other end mounted to said handle.

Preferably, said timer is an inherent timer that is a combination of said gas reservoir, said means for controlling said valve and said valve; and said predetermined time period is a cooperative result of said combination.

Preferably, said timer is a combination of said inherent timer and an external timer that is coupled with said rod and works in such a manner that said coupled rod is only allowed to move back to a rest state from an engaged one after a preset time period.

Preferably, said second device for feeding a unit drug dose of said drug powder and activating said suction-actuation mechanism comprises:

(a) a mouthpiece;

(b) means for entraining and dispersing said drug powder;

(c) means for feeding a unit drug dose of said drug powder and activating said suction-actuation mechanism;

(d) two body pieces airtight sticking together with troughs on their interface so as to accommodate rubber seal gadgets and said means for feeding drug, holes and channels in or through their bodies so as to connect with said mouthpiece and said second device and third device, cavities for storing and feeding said drug powder;

whereby said ring seal gadgets prevent said drug powder from moisture of the outside environment.

Preferably, said means for dispersing said drug powder is selected from the group comprises:

(a) a spiral gas conduit used to make spiral flow of said gas and therefore to entrain and to disperse said drug powder effectively;

(b) said gas being at an optimised angle introduced into a cylindrical cavity where said drug is and exiting said cavity in a perpendicular direction so as to produce cyclone flow of said gas and hence to entrain and disperse said drug powder effectively.

Preferably, said means for feeding a unit drug dose of said drug powder and activating said suction-actuation mechanism comprises:

(a) a dose counter;

(b) an external timer;

(c) a cylinder with a hole on one circular end in connection with said device one and a big opening at the other circular end;

(d) a piston having a rubber ring gadget mounted on its side and sliding in said cylinder;

(e) a slide or a rod having two holes at pre-designed positions and at one end being attached to or coupled with said piston via said big opening of said cylinder, being inserted into a trough between said two body pieces of said drug feeder with the other end being coupled with said dose counter and said external timer;

(f) a spring being sandwiched between said big opening and said two body pieces, used to bias back said feeding slide after being released by said external timer;

whereby one of said two holes is designed to feed said drug powder and the other is designed to open said air path for said suction-actuation mechanism so that the user can only inhale after said inhaler properly feeds said drug powder.

Preferably, said sensor or sensors that detect the changes of said gas reservoir in volume, in pressure or in both can be selected from the group comprises:

(a) a piston that can directly detect and react to the changes in both volume and pressure of said gas reservoir;

(b) a pressure gauge that can detect the change in pressure of said gas reservoir;

(c) other sensors that can detect the change in pressure of the said gas reservoir and/or the change of the position of said piston;

whereby the use of said piston as a sensor and a reactor, ie in response to the signal it senses, can simplify said inhaler and make said inhaler more compact as seen in the drawings and in the specifications.

The invention provides exemplary systems, apparatus and methods for dispersing a powdered medicament to form an aerosol and delivering it to a targeted area of a human lung. The above and other objects of the invention are realized to specific embodiments of an exemplary inhaler having a mouthpiece; a drug feeder with a drug reservoir; trigger one; valve one; a compressed gas reservoir; a sensor; trigger two; valve two; timer two; a dose counter; timer one; an air channel that is also used to deliver the drug powder; an air path that is used to actuate trigger one.

It is apparent for those skilled in the art that even from this given example, various inhalers can be made. For example the combination of the drug feeder and the mouthpiece gives the simplest dry powder inhaler, handy and ready to use. Whereas combining all the embodiments except the external timer two gives an advanced user-friendly inhaler. Considering its multi-functions such as actively dispersing a drug powder, suction actuation manner and auto-feeding a unit dose of drug powder whereas auto-locking/unlocking the actuation mechanism etc, it is still simple, robust but rich in characteristics. It is also very reliable to deliver consistent dose of drug. It makes best use of the user's inhalation and sorts out the oldest inherent coordination problem of the inhalers available today. It is universal as a result of the wide operational pressure of the gas reservoir and the corresponding reaction of T1 to the pressure in the gas reservoir.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Figure 1B:
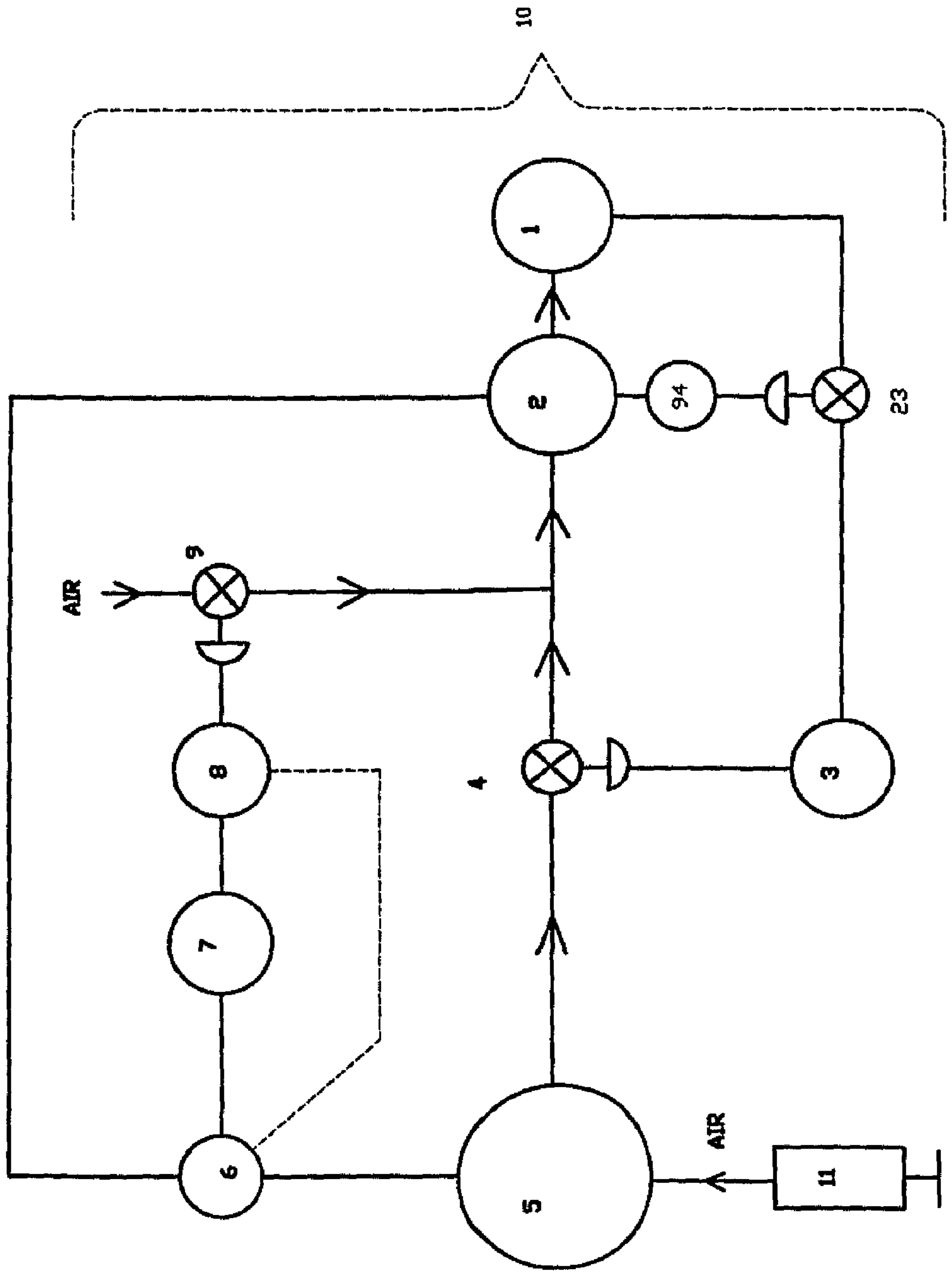
Figure 2A:
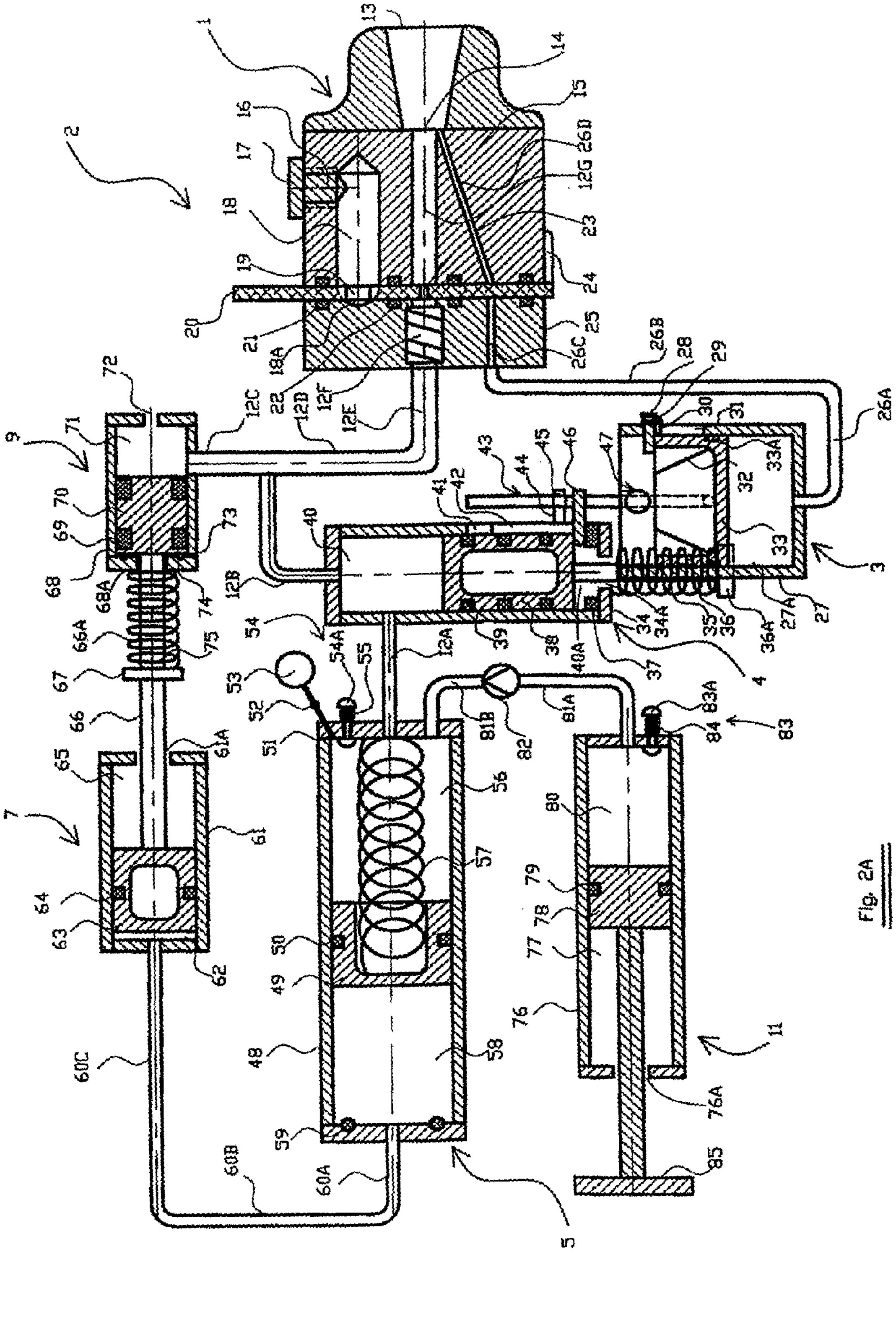
Figure 2B:
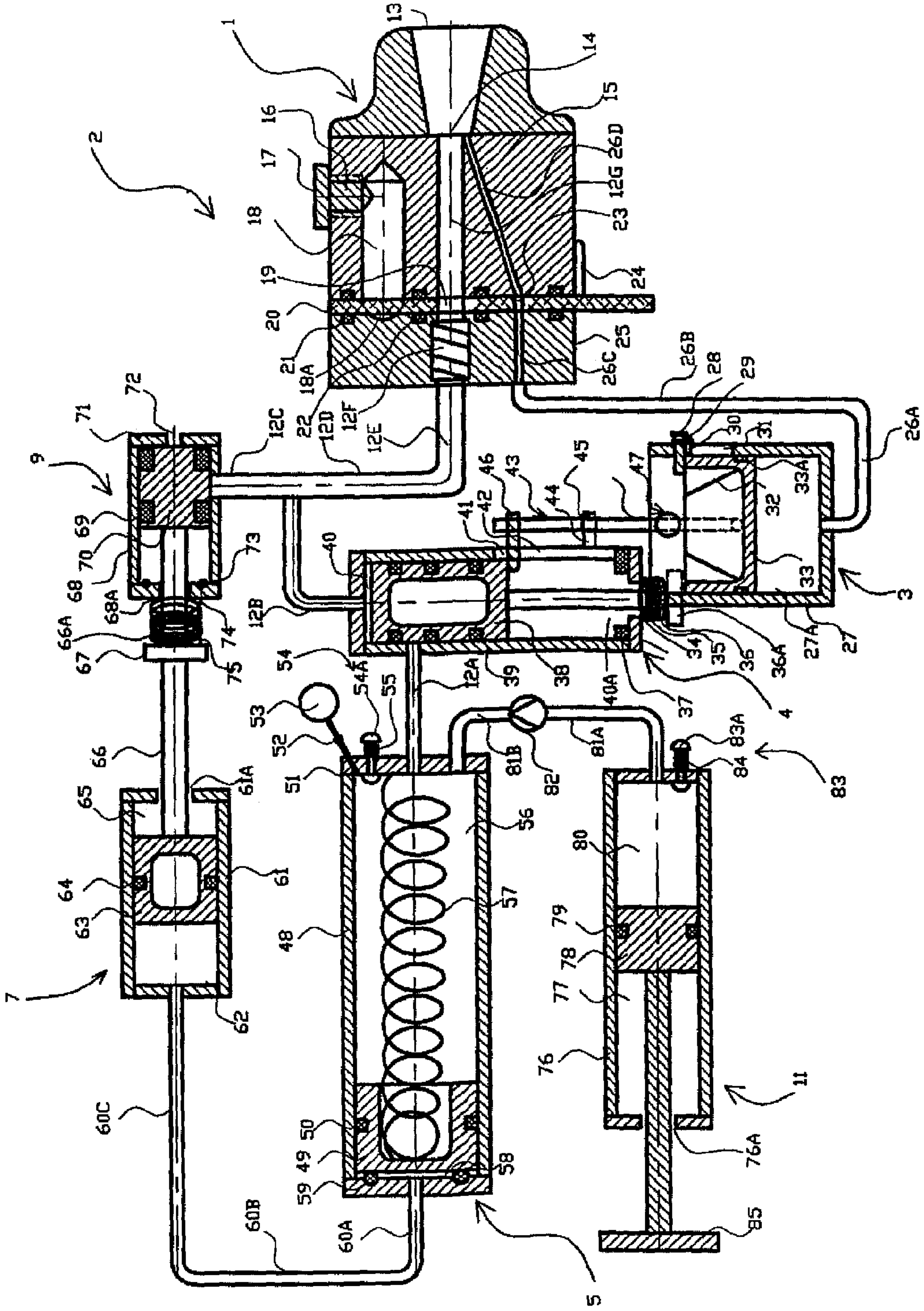
Figure 3A:
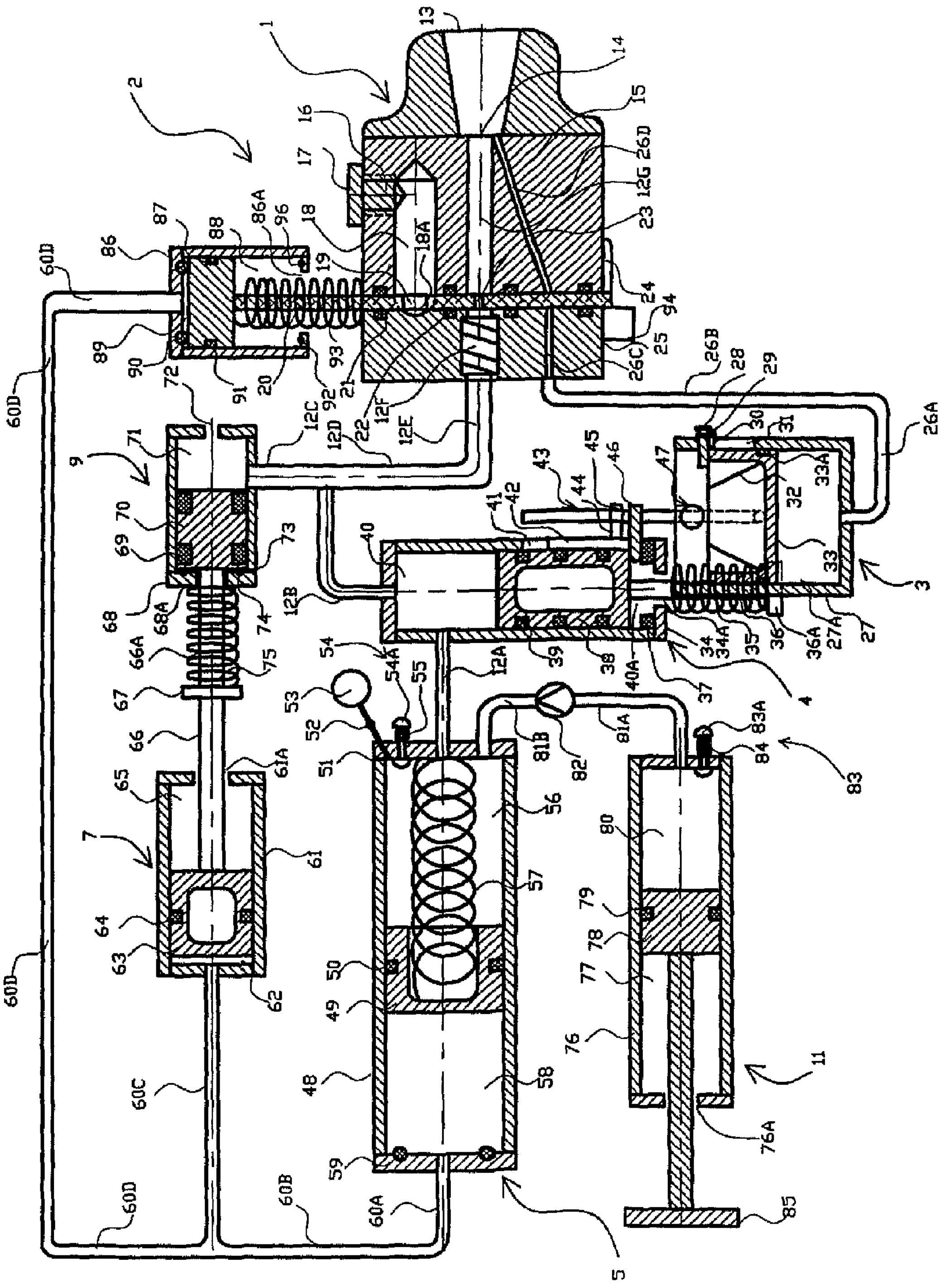
Figure 3B:
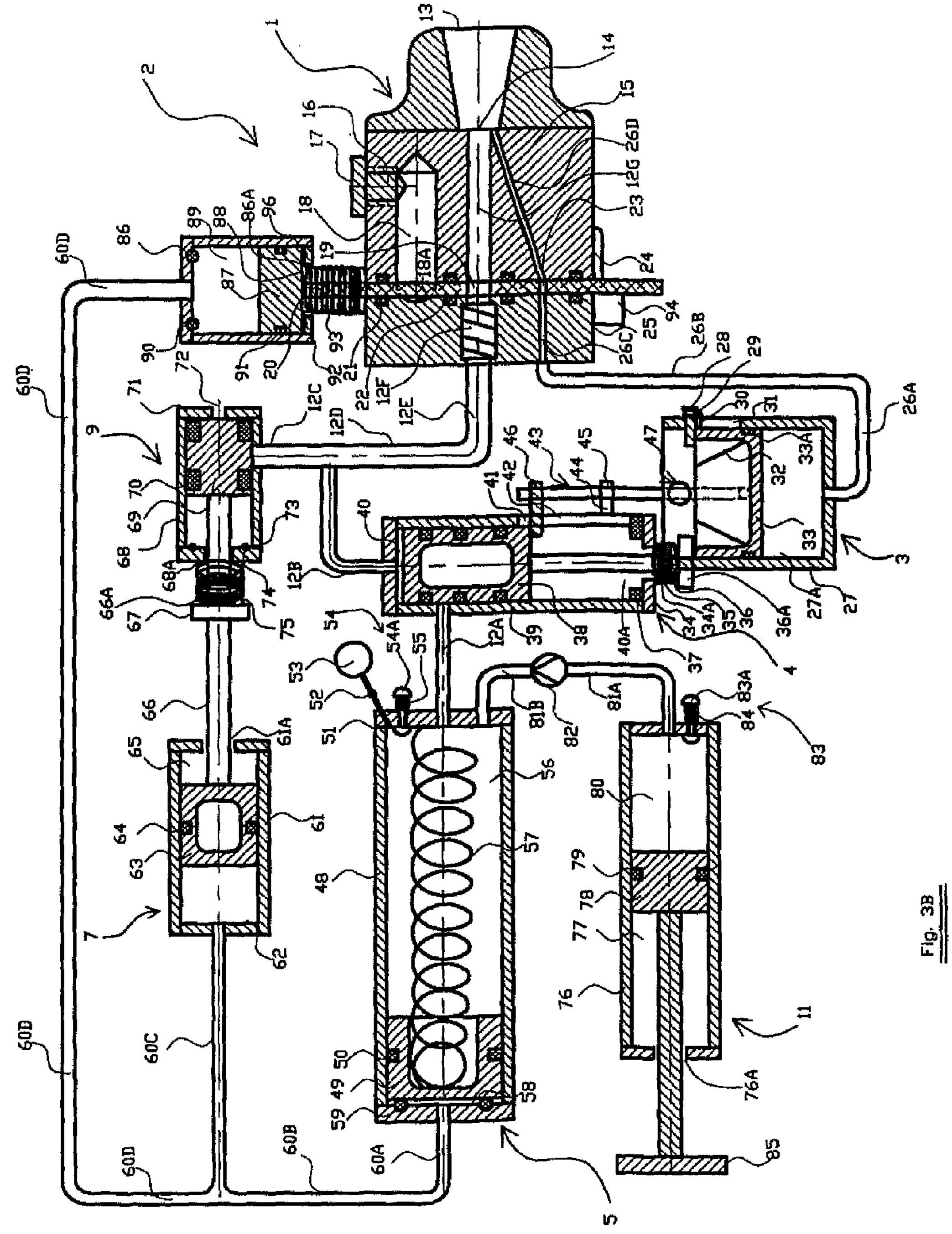
Figure 4A:
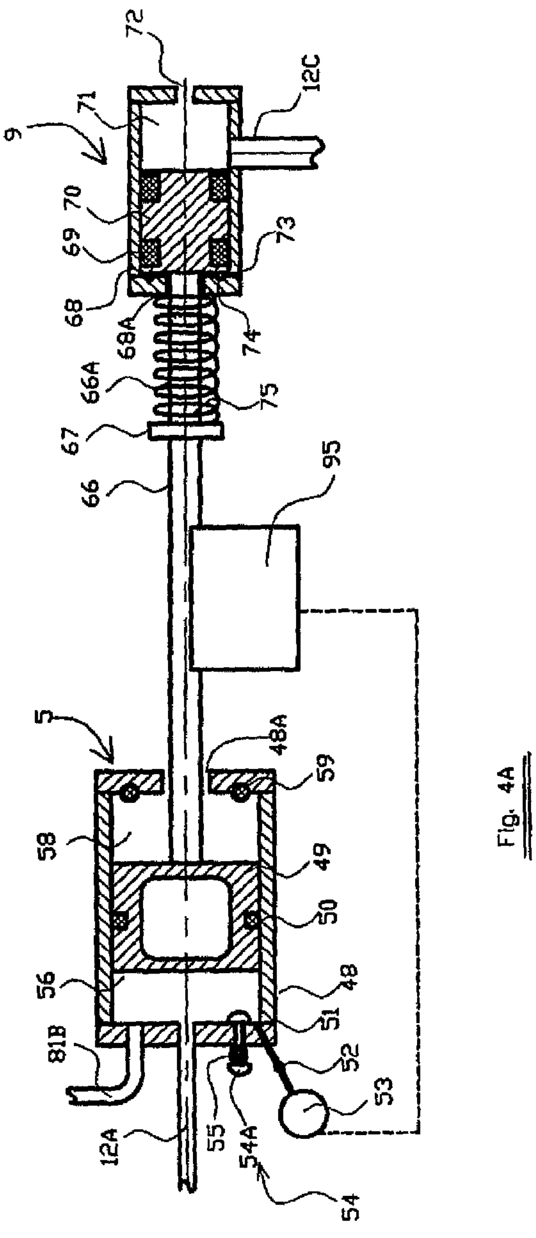
Figure 4B:
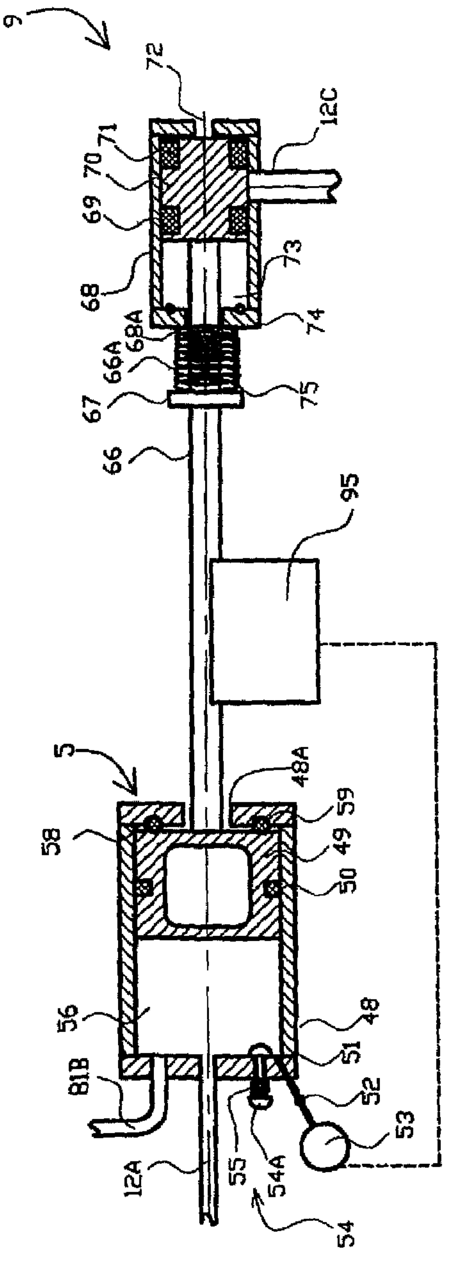
Figures 5A, 5B:
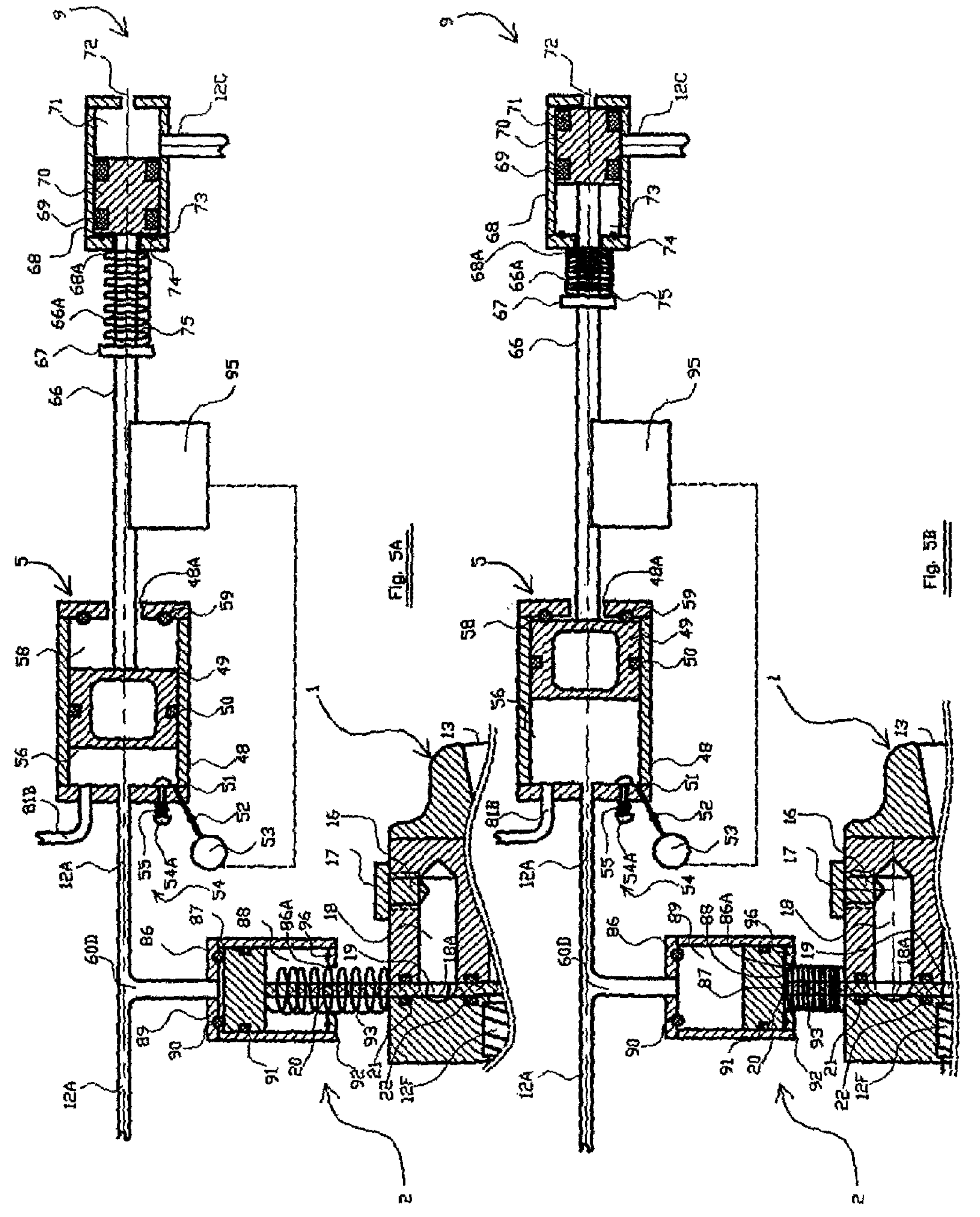
Figure 6A:
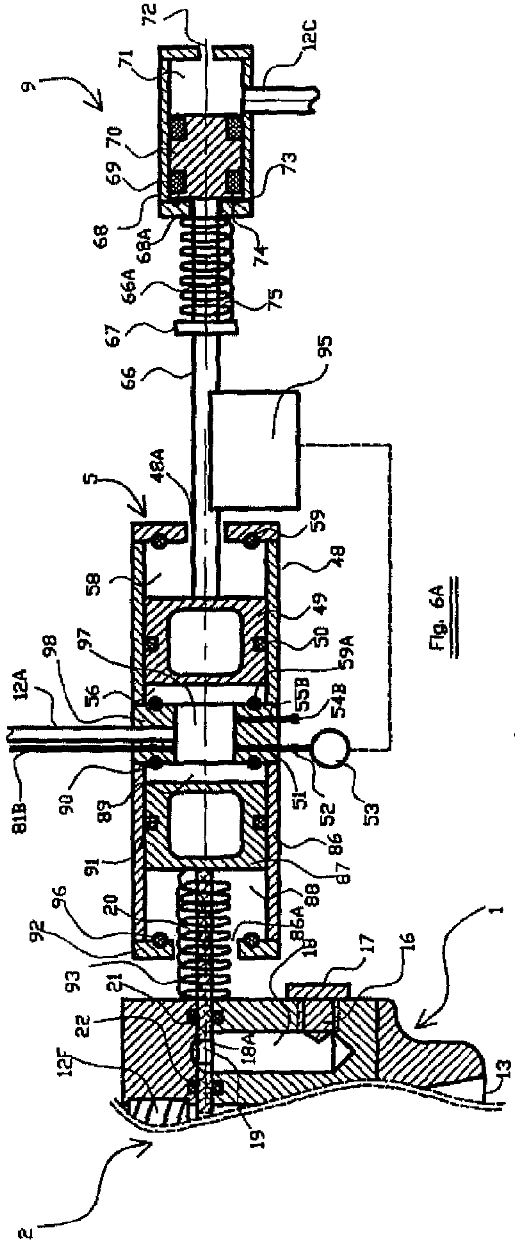
Figure 6B:
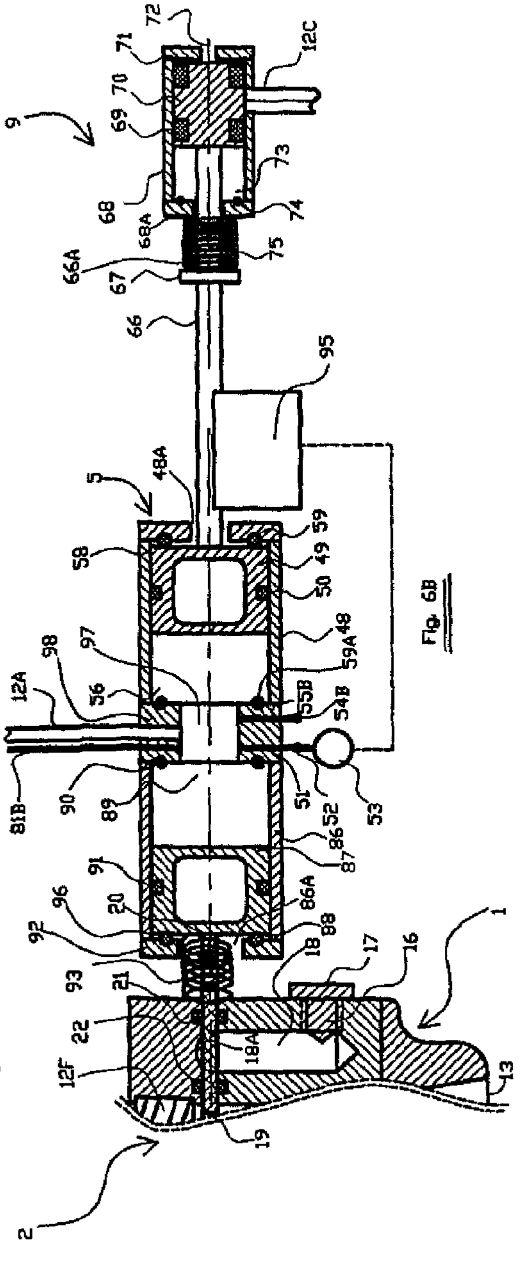
Figure 7A:
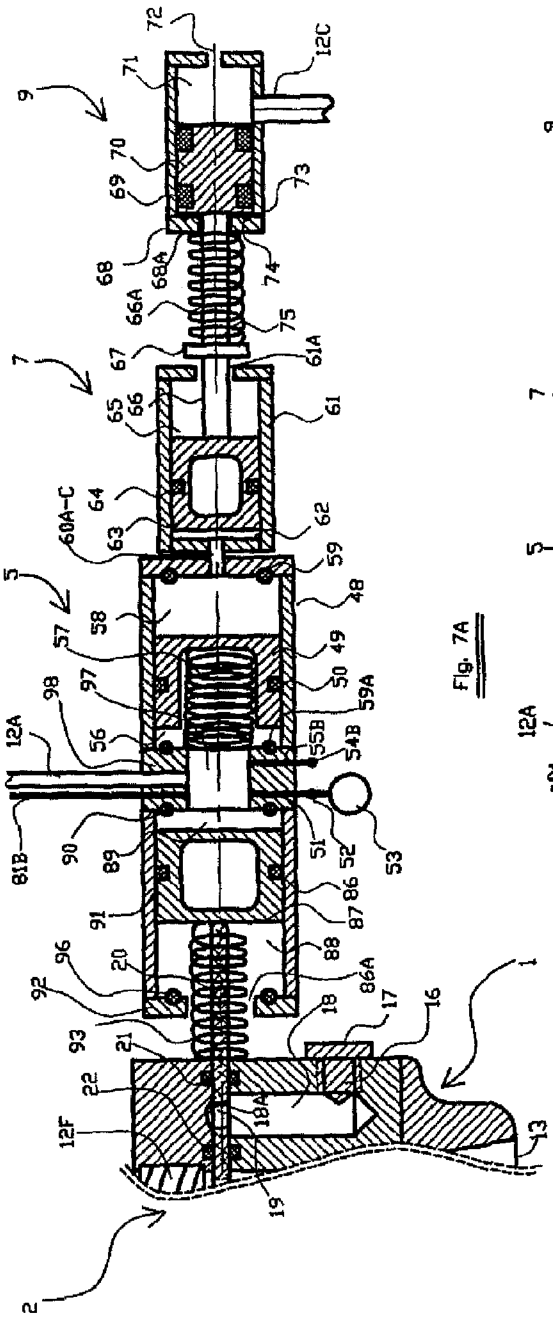
Figure 7B:
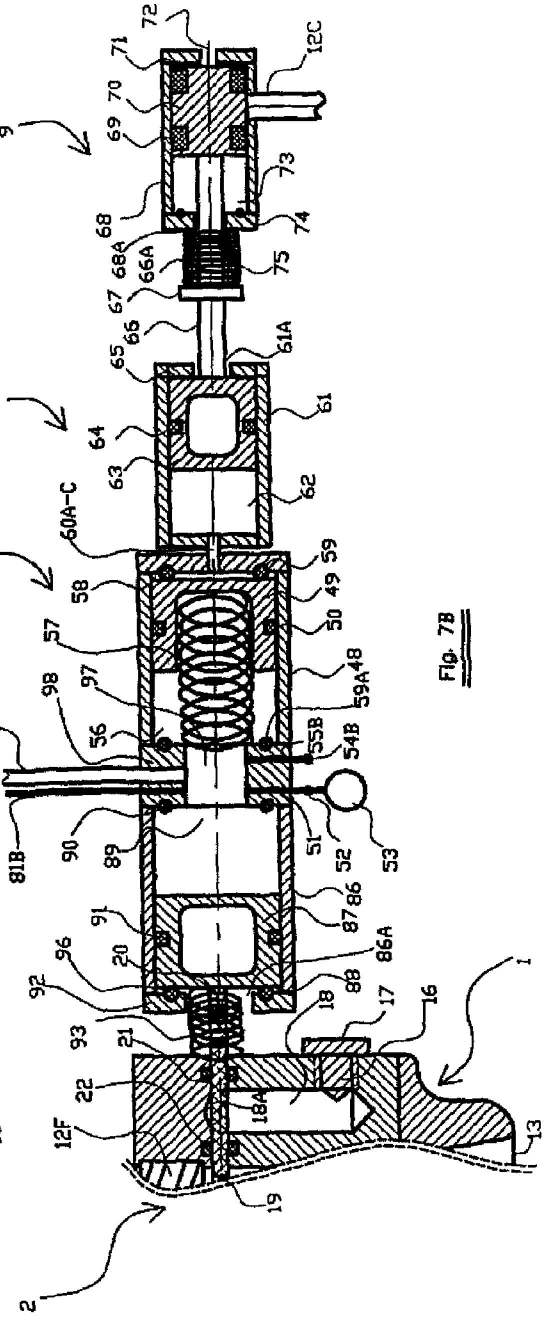
Figure 8A:
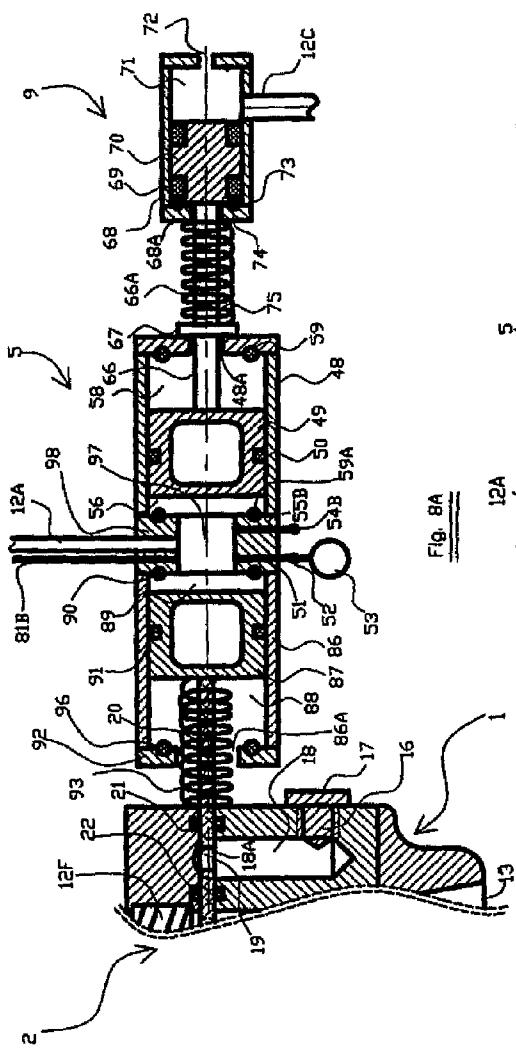
Figure 8B:
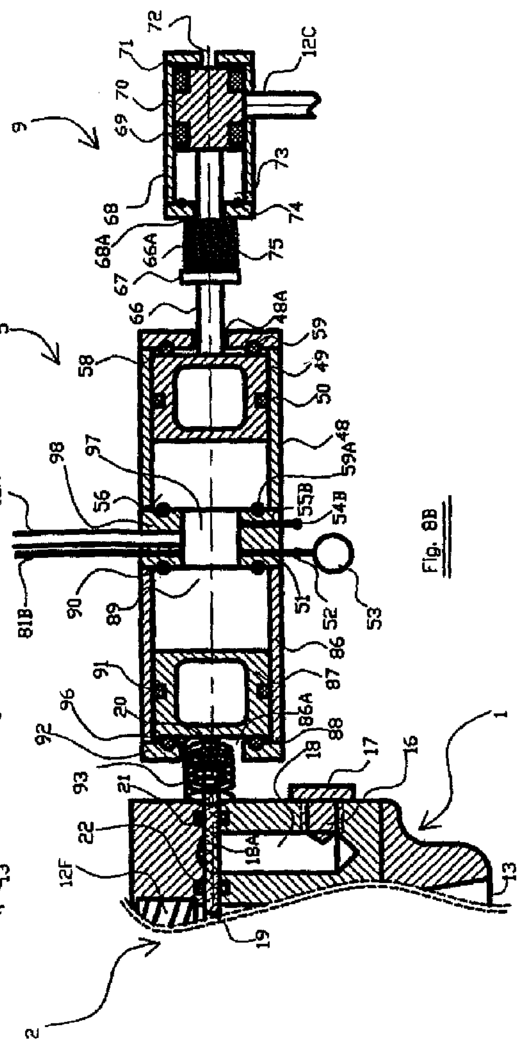
Figures 9A, 9B:
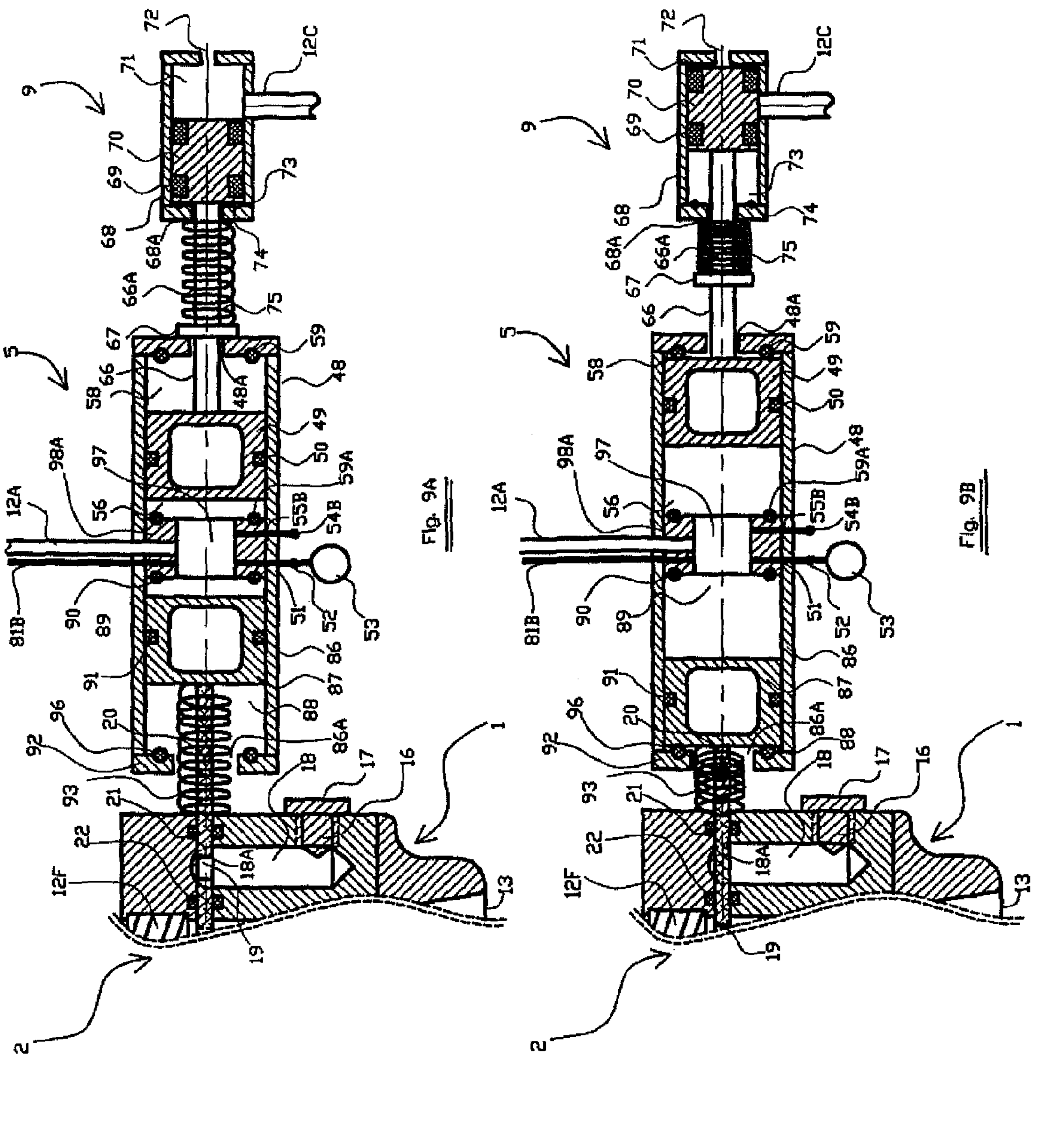
Figure 10B:
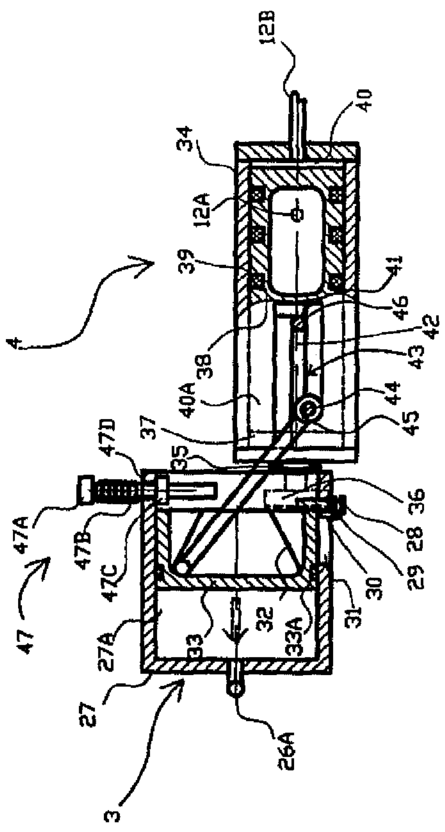
Figure 10C:
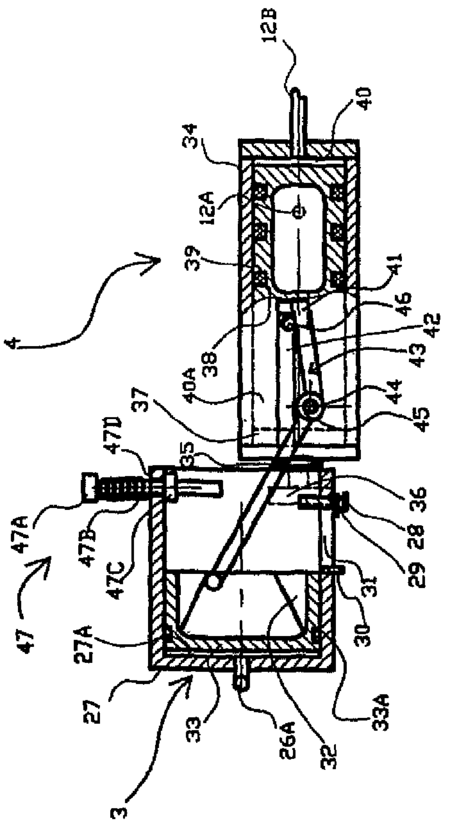
Figure 10A:
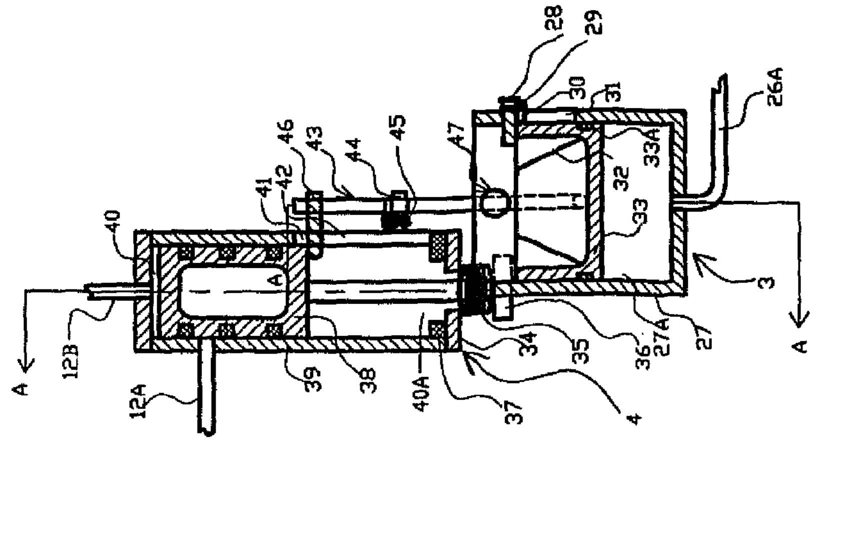
Figure 11C:
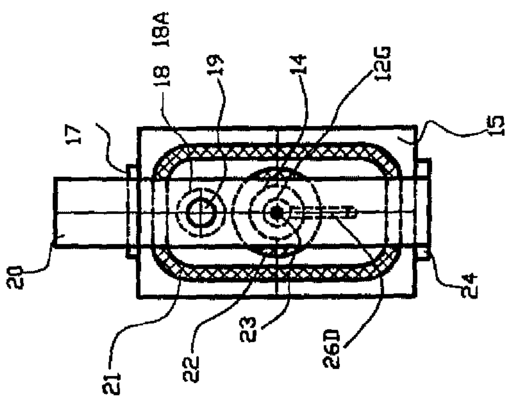
Figure 11B:
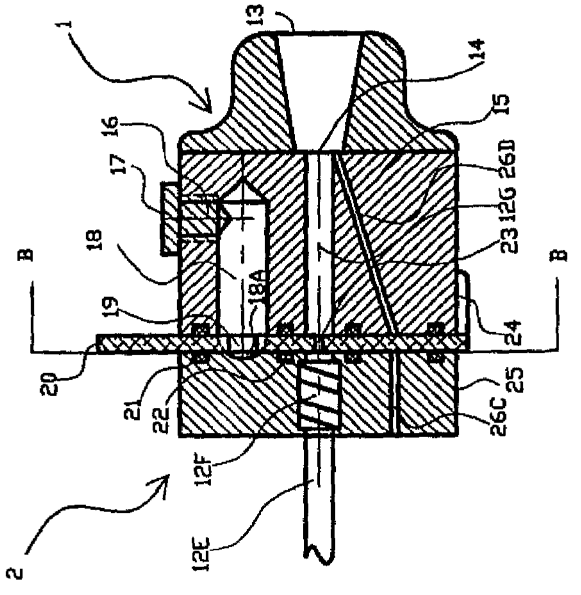
Figure 11A:
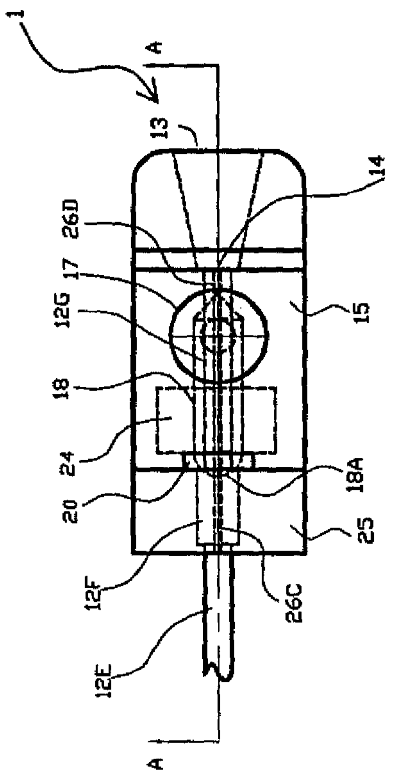
Figure 12B:
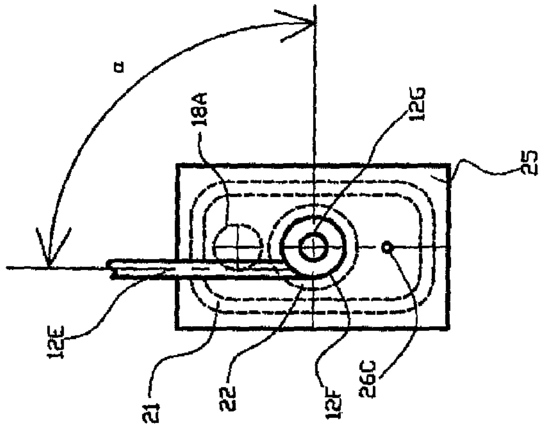
Figure 14:
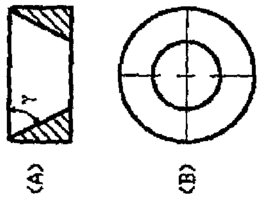
Figure 12A:
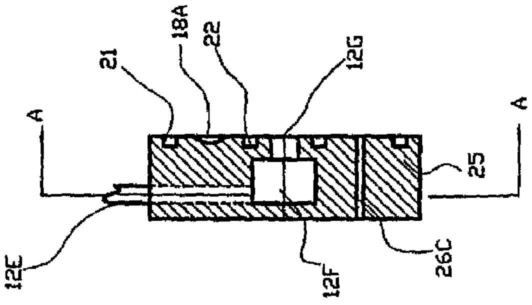
Figure 13:
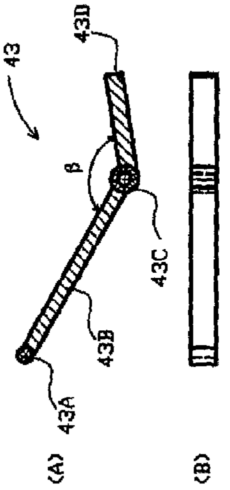

For a better understanding of the invention, and to show how embodiments of the same may be carried into effect, reference will now be made, by way of example, to the accompanying diagrammatic drawings, in which:

FIG. 1A is a schematic representation of working principle of a dry powder inhaler—a manually feeding device, FIG. 1B is a schematic representation of working principle of another inhaler—an auto-feeding device, FIG. 2A is a schematic representation of a first embodiment of a manually feeding DPI in a rest position, FIG. 2B is a schematic representation of the first embodiment of a manually feeding DPI in an engaged state, FIG. 3A is a schematic representation of a second embodiment of an auto-feeding DPI in a rest position, FIG. 3B is a schematic representation of the second embodiment of an auto-feeding DPI in an engaged state, FIG. 4A is a schematic representation of a third embodiment of a DPI with an external timer (two) in a rest position, FIG. 4B is a schematic representation of the third embodiment of a DPI with an external timer (two) in an engaged state, FIG. 5A is a schematic representation of a fourth embodiment of a DPI with external timers (one and two) in a rest position, FIG. 5B is a schematic representation of the fourth embodiment of a DPI with external timers (one and two) in an engaged state, FIG. 6A is a schematic representation of a fifth embodiment of a DPI with external timers (one and two) in a rest position, FIG. 6B is a schematic representation of the fifth embodiment of a DPI with external timers (one and two) in an engaged state, FIG. 7A is a schematic representation of a sixth embodiment of a DPI with an external timer (one) in a rest position, FIG. 7B is a schematic representation of the sixth embodiment of a DPI with an external timer (one) in an engaged state, FIG. 8A is a schematic representation of a seventh embodiment of a DPI with an external timer (one) in a rest position, FIG. 8B is a schematic representation of the seventh embodiment of a DPI with an external timer (one) in an engaged state, FIG. 9A is a schematic representation of an eighth embodiment of a DPI with an external timer (one) in a rest position, FIG. 9B is a schematic representation of the eighth embodiment of a DPI with an external timer (one) in an engaged state, FIG. 10A is a schematic representation of a sectional view of a trigger (one) in an engaged state, FIG. 10B is a schematic representation of another partial sectional view along axis A-A of FIG. 10A of the trigger (one) in an engaged state, FIG. 10C is a schematic representation of another partial sectional view along axis A-A of FIG. 10A of the trigger (one) at the releasing moment, FIG. 11A is a schematic representation of a top view of a drug feeder and a mouthpiece according to the invention, FIG. 11B is a schematic representation of a sectional view along axis A-A of FIG. 11A of the drug feeder and the mouthpiece, FIG. 11C is a schematic representation of another sectional view along axis B-B of FIG. 11B of the drug feeder and the mouthpiece, FIG. 12A is a schematic representation of a sectional view of a portion of the drug feeder, FIG. 12B is a schematic representation of another sectional view along axis A-A of FIG. 12A of a portion of the drug feeder, FIG. 13 are schematic representations of a sectional view (A) and a top view of a lever (B), and FIG. 14 are schematic representations of a sectional view (A) and a top view of a wedge (B).

EXAMPLE

Drawings - reference numerals

| No. | Name | Materials* |
|---|---|---|
| 1 | Mouthpiece | Plastic |
| 2 | Drug feeder | Metal, plastic |
| 3 | Trigger one, specially designed trigger | Metal, rubber, alloy or plastic |
| 4 | Valve one or specially designed valve | Metal, rubber, plastic |
| 5 | Gas reservoir | Metal, engineering plastic, rubber |
| 6 | Sensor or detector | |
| 7 | Trigger two, specially designed trigger | Metal, plastic, rubber, alloy |
| 8 | Timer two | |
| 9 | Valve two or specially designed valve | Metal, rubber, plastic |
| 10 | Inhaler | |
| 11 | Pump | Metal, rubber, plastic |
| 12 | 12A-G air channels | Metal, rubber |
| 13 | Big opening of the mouthpiece | |
| 14 | Mouthpiece opening to air channel | |
| 15 | Drug feeder piece one | Plastic |
| 16 | Drug refilling hole | |
| 17 | Screw | Metal, rubber, plastic |
| 18 | 18, 18A drug powder reservoir | |

-continued

Drawings - reference numerals

| No. | Name | Materials* |
|---|---|---|
| 19 | Drug feeding hole | |
| 20 | Drug feeding slide | Metal, or other conductive material |
| 21 | Rubber sealing gadget | Rubber |
| 22 | Rubber sealing gadget | Rubber |
| 23 | Air path valve | |
| 24 | Dose counter | |
| 25 | Drug feeder piece two | Plastic |
| 26 | 26A-D air path | Metal, rubber, plastic |
| 27 | Cylinder of trigger one | Metal, alloy or plastic |
| 27A | Void in cylinder 27 | |
| 28 | Bolt | Metal, alloy or plastic |
| 29 | Hook | Metal, alloy or plastic |
| 30 | Rod | Metal, alloy or plastic |
| 31 | Trough on one side of cylinder 27 | |
| 32 | Wedge or peg | Plastic |
| 33 | Piston | Metal, alloy or plastic |
| 34 | Cylinder of valve one | Metal, alloy or plastic |
| 34A | Opening of cylinder 34 | |
| 35 | Steel spring | Steel |
| 36 | Long rod | Metal, alloy or plastic |
| 36A | Handle bar | Metal, alloy or plastic |
| 37 | Rubber ring gadget | Rubber |
| 38 | Piston | Metal, alloy or plastic |
| 39 | Rubber ring gadgets | Rubber |
| 40 | Void in cylinder 34 | |
| 40A | Void in cylinder 34 | |
| 41 | Rod holding notch | |
| 42 | Trough | |
| 43 | Lever | Metal, alloy or plastic |
| 44 | Spring | Steel |
| 45 | Hinge | Metal, alloy or plastic |
| 46 | Short rod | Metal, alloy or plastic |
| 47 | Manual release button | |
| 48 | Cylinder | Metal, or engineering plastic |
| 48A | Opening of cylinder 48 | |
| 49 | Piston | Metal, alloy or plastic |
| 50 | Rubber ring gadget | Rubber |
| 51 | Tube connecting gauge | Metal, alloy or plastic |
| 52 | Valve | |
| 53 | Pressure gauge | |
| 54 | Check valve | |
| 54A | Bolt with stud | Metal, alloy or plastic |
| 54B | Valve | |
| 55 | Spring | Steel |
| 55B | Tube | Metal, alloy or plastic |
| 56 | Void in cylinder 48 | |
| 57 | Spring | Steel |
| 58 | Void in cylinder 48 | |
| 59 | Rubber ring gadget | Rubber |
| 60 | 60A-D gas tube | Metal, alloy or plastic |
| 61 | Cylinder | Metal, alloy or plastic |
| 61A | Opening of cylinder 61 | |
| 62 | Void in cylinder 61 | |
| 63 | Piston | Metal, alloy or plastic |
| 64 | Rubber ring gadget | Rubber |
| 65 | Void in cylinder 61 | |
| 66 | Rod | Metal, alloy or plastic |
| 66A | Rod | Metal, alloy or plastic |
| 67 | Spring stopping handle | Metal, alloy or plastic |
| 68 | Cylinder | Metal, alloy or plastic |
| 68A | Opening of cylinder 68 | |
| 69 | Rubber ring gadgets | Rubber |
| 70 | Piston | Metal, alloy or plastic |
| 71 | Void in cylinder 68 | |
| 72 | Fresh air inlet | |
| 73 | Void in cylinder 68 | |
| 74 | Rubber ring gadget | Rubber |
| 75 | Spring | Steel |
| 76 | Cylinder | Metal, alloy or plastic |
| 76A | Opening of cylinder 76 | |
| 77 | Void in cylinder 76 | |
| 78 | Piston | Metal, alloy or plastic |
| 79 | Rubber ring gadget | Rubber |
| 80 | Void in cylinder 76 | |
| 81 | 81A-B air tube | Metal, alloy or plastic |

-continued

| Drawings - reference numerals | | |
|---|---|---|
| No. | Name | Materials* |
| 82 | Single direction check valve | |
| 83 | Check valve | |
| 83A | Bolt with stud | Metal, alloy or plastic |
| 84 | Spring | Steel |
| 85 | Handle | Metal, alloy or plastic |
| 86 | Cylinder | Metal, alloy or plastic |
| 87 | Piston | Metal, alloy or plastic |
| 88 | Void in cylinder 86 | |
| 89 | Void in cylinder 86 | |
| 90 | Rubber ring gadget | Rubber |
| 91 | Rubber ring gadget | Rubber |
| 92 | Piston stopper | Metal, alloy or plastic |
| 93 | Spring | Steel |
| 94 | External timer one | |
| 95 | External timer two | |
| 96 | Rubber ring gadget | Rubber |
| 97 | Voids in cylinder base 98 | |
| 98 | Cylinder base | Metal, alloy or plastic |
| 98A | Cylinder base | Metal, alloy or plastic |

*Preferable materials of some parts are given, but they are not exclusive.

In the following, the same parts are provided with the same reference symbols.

DETAILED DESCRIPTION OF THE FIGURES

FIG. 1A shows a schematic working principle of a manually feeding dry powder inhaler (DPI) 10 in accordance with the present invention. The DPI 10 comprises of a mouthpiece 1, a manually feeding drug feeder 2, a trigger 3, a valve 4, a gas reservoir 5, a sensor 6, a trigger 7, a timer 8, a valve 9, a valve 23 and a pump 11.

Trigger 3 is a suction-actuated one and controlled by a user's inhalation. Valve 23 is used to control the air path between mouthpiece 1 and trigger 3. Valve 23 is coupled with drug feeder 2 in a manner that it opens only when a dose of drug powder is properly fed.

To use this DPI the user needs to fill gas reservoir 5 to a preset pressure using pump 11 after closing valve 4. Upon the increase of the air pressure of gas reservoir 5, sensor 6 receives a signal and automatically makes trigger 7 engage timer 8 and to shut valve 9. Trigger 7 controls valve 9. Timer 8 controls trigger 7. Valve 9 controls the passage of the fresh air from outside atmosphere through drug feeder 2 and mouthpiece 1 to the user's mouth. The user manually feeds the drug powder properly and at the same time opens valve 23. DPI 10 is now ready-to-use.

When the user starts to inhale from mouthpiece 1, there is no fresh air from outside atmosphere as both valve 4 and 9 are closed. Valve 4 controls the release of pressurized air in gas reservoir 5. The suction force drives trigger 3 to open valve 4 while valve 9 is still closed. The pressurized air in reservoir 5 then goes through valve 4 and into drug feeder 2 where it disperses the drug powder to form an aerosol. The aerosolised powder is then driven into mouthpiece 1 where its passage way becomes wider than that in the drug feeder. The speed of the aerosolised particles is therefore reduced. The air in mouthpiece 1 is still although the user is sucking, as there is no further supply of fresh air, which is available only after valve 9 is open. In this way the speed of the aerosolised particles is further reduced whereas the dispersion is further improved because of strong friction among the flying particles and the still air. Sensor 6 senses a signal upon release of pressurized air in reservoir 5. At a certain point, sensor 6 actuates timer 8 and drives trigger 7 to a rest state. Timer 8 holds trigger 7 for a preset time and then releases it. Valve 9 is then fully opened to allow the fresh air to get through. The aerosolised drug particles then follow with the inhaled fresh air to a targeted area in the user's lung.

After finishing inhalation, the user needs to manually set the drug feeder in a ready-to-feed state.

Although a piston pump is a preferable choice for charging the gas reservoir, other means such as a canister of compressed gas as oxygen, nitrogen or their mixtures; a canister of propellant such as HFA can also be used for the same purpose. This is suitable for all the following exemplary embodiments.

FIG. 1B shows a schematic working principle of an auto-feeding DPI 10. DPI 10 consists of a mouthpiece 1, an auto-feeding drug feeder 2, a trigger 3, a valve 4, a gas reservoir 5, a sensor 6, a trigger 7, a timer 8, a valve 9, a valve 23, a timer 94 and a pump 11.

All the elements are the same as the manually feeding version but the drug feeder and one more timer. Timer 94 is added to the auto-feeding DPI. The basic working principle is also the same except for a few points described below.

In addition to automatically make trigger 7 engage timer 8 and to shut valve 9 upon detecting the signal in reservoir 5, sensor 6 also automatically actuates a auto-feeding device in drug feeder 2 to feed the drug, to open valve 23 and to engage and actuate timer 94. Upon release of the pressurized air in gas reservoir 5, the sensor releases the auto-feeding device and put it under the control of timer 94. Timer 94 works in a manner that it will release the auto-feeding device after a preset time. During this time the user can freely inhale fresh air from the outside atmosphere after valve 9 is open. Upon release the auto-feeding device automatically goes back to a ready-to-feed state via biasing means.

A mechanical timer is a preferable one for the timer 94. However any other means that can hold the auto-feeding drug feeder at a feeding state for a while can also be used to obtain the same results. This is also true for all the following exemplary embodiments having an auto-feeding drug feeder.

Examples are given in the following for both versions of the invented DPIs.

FIG. 2A shows a first embodiment of a manually feeding DPI 10 at rest state. The DPI 10 comprises a mouthpiece 1, a manually feeding drug feeder 2, a trigger 3, a valve 4, a gas reservoir 5, a trigger 7, a valve 9 and a pump 11. A sensor 6 and a timer 8 are incorporated into other elements as clearly described in the following.

To easily understand the structure of the mouthpiece and the drug feeder, please also refer to FIGS. 11A-C. Mouthpiece 1 is a plastic moulded one with a hollow conical void in its centre. It is mounted to drug feeder 2 on one side. It has two openings 13 and 14. Opening 13 is bigger than opening 14. When DPI 10 is in use, the mouthpiece is in close contact with the lips of a user. Opening 14 is in direct connection with an air channel 12G and an air path 26D.

Drug feeder 2 comprises a body and a drug-feeding device. The body is made of plastic and includes two pieces 15 and 25. The drug-feeding device in this example is a slide 20. There is a hollow cavity 18 in piece 15 and another 18A in piece 25. The hollow cavities act as drug powder reservoir. A spiral air conduit 12F in this embodiment, used to induce a spiral flow of a gas, is integrated into piece 25. There are troughs on surfaces of piece 15 and 25. The troughs are used to accommodate a rubber seal gadget 21; another rubber seal gadget 22 and drug-feeding slide 20. A screw 17 is used to seal a drug-refilling hole 16 on piece 15. An air channel 12G, an air path 26C and an air path 26D are also integrated into both pieces 15 and 25. An integrated dose counter 24 is attached to piece 15.

Slide 20 is made of metal or alloy or other conductive materials that is compatible with the drug powder being delivered. The conductivity of slide 20 can alleviate the static electric effect on the feeding accuracy. Slide 20 has a drug feeding hole 19 and an air path valve 23 that is actually another hole. Slide 20 can slide between a forward position and a backward or recess position. At recess position, hole 19 is coaxially located in cavities 18 and 18A and it is ready-to-feed; whereas valve 23 is located in the air channel and shut air paths 26C and 26D.

Spiral air conduit 12F has an optimised diameter. It has rifling (spiral groove) on the inside of this part of the air channel. Just as its name implies spiral air conduit 12F is used to conduce the spiral follow of air through the air channel so as to fully entrain the drug powder and to effectively disperse it. At one end spiral air conduit 12F is connected with both valve 4 and valve 9 via air channels 12B, 12C and 12E. At the other end it connects with air channel 12G. Air channel 12G directly connects opening 14 of mouthpiece 1.

The rubber seal gadgets 21 and 22 are used to make the drug storage cavities 18 and 18A airtight from the outside atmosphere so that there is no air leakage from the interface of the pieces 15 and 25. They also prevent the drug powder from the moisture in the outside environment. Screw 17 is normally used to seal drug storage cavity 18. Hole 16 is used to refill drug powder by removing screw 17 when necessary. Cavity 18 is a drilling hole in piece 15 whereas cavity 18A is a half hollow globe in piece 25. They are coaxially aligned when these two pieces fixed together. Dose counter 24 is a mechanical or an electrical one that uses the movement of slide 20 to count the doses. It is only actuated once when slide 20 moves forward and backward once. Air path 26C is a drilling hole in piece 25 whereas 26D is another hole in piece 15. At one end air path 26C connects with trigger 3 via air paths 26A and 26B and the other end with air path 26D via valve 23. Air path 26D directly connects mouthpiece opening 14 at the other end.

Although it is preferable that a hole in slide 20 acts as valve 23, other means of controlling the air path can also be used for the same purpose. For example, a mechanical or an electrical valve coupled with slide 20 can easily be adapted for opening and closing the air path corresponding to the forward and backward positions respectively.

Refer also to FIGS. 10A-C, trigger 3 mainly comprises of a cylinder 27 or cylinder three, a piston 33 or piston three, a lever 43 and a hand-release button 47. On one circular end cylinder 27 connects drug feeder 2 via a void 27A, air paths 26A and 26B. The other circular end of cylinder 27 is open. On one side of cylinder 27 there is a hand-release button 47 close to the open end. Hand-release button 47 comprises of a long bolt with a stud on top 47A, a spring 47B and a nut 47C (Refer to FIG. 10B). It is accommodated in a hole 47D on the side of cylinder 27. Hole 47D is just located over one arm of lever 43. On other side of cylinder 27 is a screw 28 with a pivoted hook 29. A trough 31 with a dimension less than the diameter of screw 28 is aligned with screw 28. Hook 29 is used to keep piston 33 steady at rest state by working together with a short rod 30 attached on one side of piston 33. Rod 30 has a diameter less than the width of trough 31 so that it can slide along the trough.

Piston 33 has one circular end closed and the other end open. A wedge 32 is inserted into the cavity of the piston 33 from the open end. Wedge 32 is used to transform a horizontal force to a vertical one as shown in FIG. 10C and described in detail later. A rubber seal gadget 33A is used to make piston 33 airtight. Lever 43 has two arms 43B and 43D (Refer to FIG. 13). A small ball 43A is attached to the top of arm 43B so as to reduce the friction between lever 43 and wedge slope 32. The two arms joint with each other via a circular tube 43C at an optimised angle. The lever can therefore be pivotably mounted to a hinge 45 of valve 4 as described later. The angle between these two arms ranges in 1-359 degree, preferable between 45-250 degree and best between 70 and 120 degree (Refer to the angle β shown in FIG. 13).

The structure of wedge 32 is shown in FIG. 14. The angle γ ranges from 5 to 85 degree, preferably from 20 to 75 degree and most preferably from 40 to 60 degree.

Although a piston with an integrated wedge is a preferable configuration for the trigger one, other means such as a rod attached to or coupled with a piston or a flexible diaphragm can also be easily adapted and used for the same purpose.

Valve 4 is a specially designed valve and mainly comprises a long rod 36 with a handle bar 36A attached to a piston 38, a spring 35, a cylinder 34, a rubber gadget 37, and rubber ring seal gadgets 39 mounted on piston 38. On one circular end of cylinder 34 is a hole in connection with valve 9 and drug feeder 2 via air channels 12B-E. On the other end of cylinder 34 is a circular opening 34A that is big enough to allow rod 36 to move freely. On one side of cylinder 34 is a hole in connection with gas reservoir 5 via air channel 12A. On another side of cylinder 34 are a trough 42 and a notch 41. Trough 42 is a long narrow one whereas notch 41 is perpendicular to trough 42. Trough 42 is just wide enough for a short rod 46 to slide freely. Notch 41 is just wide enough to accommodate rod 46. Hinge 45 is attached to cylinder 34 at a suitable position below trough 41. Hinge 45 is used to accommodate lever 43 and a biasing spring 44 used to bias lever 43 to the rest state.

Spring 35 sandwiched between opening 34A and handle bar 36A is used to bias piston 38 in rest state and makes valve 4 open. Rods 46 and 36 are attached to one circular end of piston 38 so that the user can manually engage valve 4.

Although the cylinder and the piston is preferably selected to act as a valve to control the release of the compressed gas in gas reservoir 5, other means such as a mechanical or an electrical valve can also be chosen to do the same work.

Gas reservoir 5, or a gas container, mainly comprises a cylinder 48, a piston 49 with a rubber ring sealing gadget 50, a spring 57 and a rubber ring gadget 59 used to seal one circular end of cylinder 48. On one circular end of cylinder 48 there is a hole in connection with trigger 7 via air tubes 60A-C. On the other circular end of the cylinder there are four holes. Three of them are in connection with valve 4 via the air channel 12A; pump 11 via an air tube 81B, a single direction check valve 82, air tube 81A; a pressure gauge 53 via a tube 51 and a valve 52 respectively. The fourth is used to accommodate a check valve 54 acting as a manual release button that comprise of a spring 55 and a bolt 54A with studs on both ends. However this manual release button can be in forms other than the simplest example given here such as a valve 54B and a tube 55B shown in FIGS. 6A and 6B etc. The release button is used for checking inhaler 10. Piston 49 can slide in cylinder 48. One of its circular ends is open to accommodate attached spring 57 whereas the other end is enclosed. Spring 57 attaches to an inside surface of one circular end of cylinder 49 too. At rest state the spring biases piston 49 at a preset position of cylinder 48. Piston 49 divides cylinder 48 into two separated voids 56 and 58 having volume V1 and V2 respectively. At rest state the effective volume of reservoir 5 is equal to V1.

Trigger 7 is specially designed and comprises a cylinder 61, a piston 63 and a rod 66. At its one circular end cylinder 61 has one hole in connection with gas reservoir 5 via air tubes 60A-C. At the other end it has a circular opening 61A so as rod 66 attached to one end of piston 63 can move freely. At the other end rod 66 is mounted to a spring stopping handle 67. Piston 63 can slide inside cylinder 61. At rest state, it divides the cylinder into two voids 62 and 65. A rubber ring seal gadget 64 mounted on piston 63 is used to make cylinder 61 airtight.

Although a cylinder with a piston is given as an example here for trigger 7, it is apparent for a skilled in the art that other means such as a normal mechanical trigger, an electrical controlled trigger, and a combination of a piston with a diaphragm etc., which react to the change or changes in pressure or in volume or in both of gas reservoir 5, can also easily be adapted to act as trigger 7. Another example is given later in this disclosure of the invention.

Valve 9 is another specially designed valve and comprises a cylinder 68, a piston 70, a rod 66A, rubber ring gadgets 69, a spring 75 and another rubber ring gadget 74. Cylinder 68 has two voids 71 and 73 separated by piston 70. At one side cylinder 68 has one hole in connection with valve 4 and drug feeder 2 via air channels 12B-E. At one circular end it also has a hole 72 connecting the outside environment. The user of inhaler 10 can only inhale fresh air from the atmosphere via hole 72. At the other circular end of cylinder 68 is a circular opening 68A accommodating rod 66A. Rod 66A attaches to or couples with piston 70 at one end. It is mounted to spring stopping handle 67 at the other end. The cylinders 61, 68, the rods 66 and 66A, spring stopping handle 67 and spring 75 are aligned coaxially.

Valve 9 described above is a preferable embodiment of such a valve. However other means acting as a valve to control the intake of fresh air by the user can be also used here to get the same results. For example, a ball attached to a rod in combination with a diaphragm having holes at proper positions can be adapted as a valve, Pump 11 comprises a cylinder 76, a piston 78, a handle with a rod 85 and a single direction check valve 83 including a bolt 83A with a stud on one end and a spring 84. Cylinder 76 has an opening 76A at one circular end to accommodate the rod attached to handle 85. It has two holes at the other circular end. One is in connection with gas reservoir 5 via air tube 81A, check valve 82 and air tube 81B. The other hole is just used to accommodate check valve 83.

A piston style pump is preferably used to charge gas reservoir 5, as it uses the air as source of the compressed gas. However other means such as a canister of compressed gas as nitrogen, or oxygen, or their mixture, or air; a canister of propellant such as hydro fluorocarbons can also be used to charge gas reservoir 5.

In this embodiment, sensor 6 is piston 49 whereas timer 8 is very unobvious. Piston 49 not only detects the changes in both the pressure and the volume of gas reservoir 5 upon charging or releasing of a compressed gas, but also reacts to these changes by moving between a rest position and a fully engaged state as described in detail later. Timer 8 is inherently incorporated into air reservoir 5, trigger 7 and valve 9 as described in the following. Timer 8 is called an inherent timer in such an embodiment of inhaler 10.

FIG. 2B shows the schematic representation of the first embodiment at engaged state.

To engage DPI 10, the user first manually shuts valve 4 by pushing handle bar 36A forward. At the end of trough 42, rotate the handle to put rod 46 into notch 41. Rubber ring gadgets 39 are now in a position separating air channel 12A and 12B so that reservoir 5 is now enclosed. The user then pumps air into void 56 of gas reservoir 5. The increased pressure P1 in void 56 drives piston 49 to expel the air in void 58 to void 62 via air tube 60A-C. Piston 63 then moves to the right in the diagram as the pressure P2 in void 62 increases. This movement continues to drive piston 70 to the left until the piston 70 blocks fresh air inlet 72 and air channel 12C. Pistons 63 and 70 stop moving upon further pumping air into void 56. Void 62 now has a pressure $P_2$*. At this moment the driving force to move piston 63 $A_2 \times (P_2^* - P_a)$ is just equal to the biasing force F of spring 75, where $A_2$ intersectional area of cylinder 61 & $P_a$ atmosphere pressure. It is desirable that piston 49 is still not in touch with rubber ring gadget 59 at this moment. Further pumping air into void 56 drives piston 49 to compress rubber ring gadget 59. The air in void 62 having a volume V3 at this state is further compressed to reach a value higher than $P_2$*. Further pumping air into void 56 to a preset value P. The total volume of the pressurized air in gas reservoir 5, or the effective volume of gas reservoir 5 for containing the compressed gas at engaged state, is now the sum of V1 and V2 as a result of the reaction or the movement of piston 49 in response to the increase in the gas pressure. From this point of view piston 49 is not only a sensor but also a functioning reactor, ie in response to the signal it senses. Rubber ring gadget 59 is used to seal gas reservoir 5 when its pressure is high. Such a configuration has obvious advantages of giving inhaler 10 a wide range of operational pressure; therefore it is adjustable to suit different drug powder formulations so as to get an optimised aerosol.

The user then manually feed the drug by pushing the top end of slide 20 fully inside the body of drug feeder 2. Drug feeding hole 19 is put between air channels 12F and 12G along with a fixed volume of drug powder. Acting as a valve hole 23 is positioned between air paths 26C and 26D. Inhaler 10 is now ready-to-use.

Upon the user's inhalation, there is no air from air channel 12G because both valve 4 and 9 are shut. Only air paths 26A-D are open. The user's suction produces negative pressure in a void 27A of cylinder 27 (Refer to FIG. 10A, FIG. 10B). Piston 33 and the attached wedge 32 move along the dashed arrow direction. This movement drives lever arm 43B downward in FIG. 10B. The other arm 43D correspondingly moves upward. Short rod 46 is forced to move upward too. At certain point as shown in FIG. 10C, Rod 46 is released from notch 41. It slides back to void 40A along with piston 38 driven by the biasing force of spring 35. Once piston 38 passes air channel 12A, valve 4 is open. The pressurized air in gas reservoir 5 rushes into void 40 of cylinder 34. The coming air causes an increase in the pressure of void 40, which in turn helps to bias piston 38 to rest state. Such a configuration guarantees the quick release of the compressed gas in gas reservoir 5 so as to disperse the drug powder properly.

The compressed air only goes to the drug feeder via air channels 12B, 12D and 12E, because air channel 12C is shut by valve 9 at this moment. At air channel 12F, the compressed air is forced to flow spirally. The spiral airflow entrains the drug powder, aerosolises the powder particles and then brings the aerosol to the mouthpiece. The speed of the particles is reduced as the air thereof is still and the area of the air channel thereof is much bigger than that of air channel 12G.

Now it is high time to explain the incorporated unobvious inherent timer 8.

Upon release of the compressed gas in reservoir 5, the pressure in void 56 decreases. When the pressure is too low to balance the biasing force of spring 57, piston 49 moves right in FIG. 2B. Correspondingly the pressure in void 62 decreases. Piston 63 does not move until the pressure in void 62 is lower than $P_2$*. Once piston 63 moves leftward in FIG. 2B, it brings piston 70 leftward too. Valve 9 will only open after piston 70 passes air channel 12C and makes fresh air inlet 72 in connection with air channel 12C via void 71 of cylinder 68. Then the fresh air will be inhaled through air channels 12C, 12D, 12E, 12F, 12G and mouthpiece 1. The inhaled fresh air brings the aerosolised particles into a targeted region in the user's lung.

Timer 8 is therefore the combination of gas reservoir 5, trigger 7 and valve 9. The total time delay (or time interval) from the release of the pressurised air in gas reservoir 5 to the opening of valve 9 is a cooperative or a joint effect of these elements of inhaler 10. It has two parts. The first part T1 is the time for the pressure in void 62 to decrease to $P_2$*. The second part T2 is the time for piston 70 to pass air channel 12C. T1 is dependent on the preset pressure P of the gas reservoir and the maximum biasing force of spring 75 at an engaged state. T2 is dependent also on the biasing force of spring 75, the movement of piston 70 in cylinder 68 and the distance between fresh air inlet 72 and air channel 12C. During the total time period T, the speed of the aerosolised powder particles in the mouthpiece is reduced; considering the time for spherical unit density particles of 1 to 10 μm to reach their terminal settling velocity is in $10^{-5}$ to $10^{-3}$ s, respectively. The term 'terminal settling velocity' is the speed of a falling particle in a gravity field without external forces, at which the aerodynamic drag force is equal to the gravity.

It is apparent for a skilled in the art that the higher the P is, the longer the T1 will be. It is also apparent for a skilled in the art that the higher the P is, the better the aerosolisation will be and the faster the drug particle will fly for a given powder. The increase in T1 will slow down the fast flying particles. Such an inherent feedback mechanism of T1 to P has a great advantage of alleviating the side effect of the high P in the gas reservoir. It also makes the inhaler more flexible and more universal.

It is also very clear that there is no user's inhalation wasted on actuating a valve or a trigger. After taking a medicament, the user manually sets the inhaler back to rest state.

FIG. 3A shows a schematic representation of a second embodiment of a DPI 10 with an auto-feeding device at rest state. It is based on the first embodiment. All the others are the same as those shown in FIG. 2A and FIG. 2B except for drug feeder 2 having an auto-feeding device. Hereafter only the new features are described.

The auto-feeding device comprises a cylinder 86, a piston 87, void spaces 88 and 89 in cylinder 86; rubber ring gadgets 90, 91 and 96, a circular piston stopper 92, a spring 93 and drug feeding slide 20. At one end slide 20 is attached to or coupled with piston 87. Rubber ring gadget 96 is embedded into cylinder stopper 92 so as to secure the airtight property of cylinder 86 when inhaler 10 is in an engaged state. An external timer 94 is coupled with drug-feeding slide 20 and attached to drug feeder 2. It is actuated by drug-feeding slide 20. Once it is engaged, it holds drug feeding slide 20 and only releases it after a preset time. It is apparent for a skilled in the art to use the movement of slide 20 to engage and to actuate external time 94 at the same time.

At one circular end cylinder 86 is in connection with gas reservoir 5 and trigger 7 via air tubes 60A-D. At the other end it has an opening 86A with inserted piston stopper 92. The distance between the top surface of piston stopper 92 and the lower circular end of piston 87 is equal to that between the central lines of drug-feeding hole 19 and valve 23. Drug feeding slide 20 is attached to or coupled with the lower end of piston 87. Rubber gadgets 91, 96 are used to seal the piston whereas rubber ring gadget 90 is used to reduce the noise when spring 93 biasing back piston 87 from engaged state.

FIG. 3B shows a schematic representation of the second embodiment of DPI 10 with an auto-feeding device at engaged state. Upon pumping air into gas reservoir 5, piston 87 moves in a similar way as that of piston 63. When it is pushed fully to touch rubber ring gadget 96 attached to piston stopper 92, void 89 now has a volume V4. In this embodiment of inhaler 10, V2 must be bigger than the sum of V3, V4 and V5 that is the total volume of free spaces in tubes 60A-D so as to provide the driving force for valve 9 and the auto-feeding device. Slide 20 moves along with the movement of piston 87. It automatically feeds the drug, engages and actuates timer 94 and dose counter 24. Timer 94 holds slide 20 for a preset time and then releases it. Spring 93 then biases piston 87 back to rest state. The preset time is longer than a normal inhalation needed such as longer 10 seconds, preferable between 25 to 258 seconds.

It is preferred that timer 94 is a mechanical one. However it can also be other means of holding slide 20 for a while such as an electrical device. For example, in the simplest case timer 94 is just a latch attached to the body of drug feeder 2. It automatically holds slide 20 in the engaged state once it is activated until it is manually forced to release the slide. In another example timer 94 can be a modification of a kitchen-timer, cheap and reliable and also available.

It is apparent for a skilled in the art that all the other elements react in same manners as described in the first embodiment shown in FIGS. 2A and 2B.

FIG. 4A shows a third embodiment of a manually feeding inhaler 10, based on the first embodiment, at rest state. In this case, cylinder 61, piston 63, air tubes 60A-C and rubber ring gadget 64 of trigger 7 in the first embodiment are completely removed from inhaler 10. Their functions are replaced by piston 49 in gas reservoir 5, rod 66 and an external timer 95. Rod 66 acts as trigger 7. Cylinder 48 is modified at one circular end. Instead of a small hole there is a big opening 48A so as to accommodate rod 66 that is attached to or coupled with piston 49. From this point of view piston 49 is not only a sensor in this embodiment but also a multi-functioning reactor. In response to the increase in the gas pressure, it not only changes the effective volume of the gas reservoir but also engages valve 9 via the attached or coupled rod 66. All the others are the same as in the first embodiment.

Timer 95 is coupled with rod 66. In this embodiment the pressure gauge is not only used to check inhaler 10 but also to actuate timer 95 when the pressure in gas reservoir 5 drops to a preset value $P_s$. After being actuated, timer 95 holds rod 66 for a preset time T3 and then releases it. Spring 75 biases rod 66 to the rest state along with the elements attached directly or indirectly with it. In this case the time interval between the release of the compressed gas to the opening of valve 9 is equal to the sum T2, T3 and a T4. T4 is the time for the pressure in the air reservoir 5 to drop from P to $P_s$. T4 has a similar relationship with the P as the T1 does.

FIG. 4B shows a representation of the third embodiment of manually feeding inhaler 10 at engaged state. Upon pumping air into gas reservoir 5 to a preset value P, piston 49 moves to the left until it compresses rubber ring gadget 59. It also drives rod 66 to the left in the diagram to engage timer 95 and to close valve 9. When the air pressure in gas reservoir 5 drops after valve 4 is suction-actuated, piston 49 is not biased back immediately but only moves after a time period equal to the sum T3 and T4. Valve 9 thereafter is opened after another time interval of T2. All the other elements react in the same manners as those described in the first embodiment and will not be repeated here.

Comparing to the first embodiment, this example offers much more driving force to close valve 9. Inhaler 10 can also be made more compact than the first embodiment.

FIG. 5A shows a representation of a fourth embodiment—an inhaler 10 with an auto-feeding device at rest state. This model is based on the second and third embodiments. Trigger 7 is the same as shown in the third embodiment whereas the auto-feeding drug feeder 2 is the same as shown in the second embodiment. FIG. 5B shows us its engaged state. The auto-feeding device directly connects to gas reservoir 5 via air tube 60D that is a branch of air channel 12A. Valve 4 is controlled directly from rod 66 connecting or coupling with piston 49 in cylinder 48. This embodiment has the advantage over the second embodiment at offering more driving forces for the auto-feeding device, because it uses the high-pressure gas as driving force. In this case gas reservoir 5 has a total volume of the sum of V1, V2 plus V4 when it is in the charged state. The operational procedures are apparent to a skilled in the art and will not be repeated here.

FIG. 6A shows a representation of a fifth embodiment at rest state. This model is a further modification of the fourth embodiments. FIG. 6B shows us its engaged state. In this embodiment cylinders 49 and 86 are coupled together via a cylinder base 98 having a void 97 of volume V5. A rubber ring gadget 59A is embedded into one end of cylinder base 98. It is used to reduce the noise in case of piston 49 hits the cylinder base. The total volume of gas reservoir 5 is the sum of V1, V2, V4 and V5 when charged. Tubes 12A, 81B and 51 all connect gas reservoir 5 via cylinder base 98. Check valve 54 is replace by a normal mechanical valve 55B and a tube 54B. Rubber ring gadget 96 is embedded into cylinder stopper 92 so as to secure the airtight property of cylinder 86 when inhaler 10 is in the engaged state. It acts in a similar way as rubber ring gadget 59 in cylinder 48. Such a configuration again guarantees that inhaler 10 has a wide range of operational pressure.

The operational procedures are apparent for a skilled in the art and will not be repeated here. Comparing to all the other models described above, this one is more compact.

A cylindrical shaped cylinder base 98 is a preferable embodiment. However it can also be other shapes such as a cubic or other shaped polyhedron, having a void in the centre, which is used as a compressed gas reservoir and means for connecting all coupled devices, a plurality of holes on a surface or surfaces that are used to connect or communicate with other devices and/or some accessories such as a pressure gauge, a check valve, a piston pump etc if necessary.

FIG. 7A shows a representation of a sixth embodiment—an auto-feeding inhaler 10 at rest state. This model is modified from the fifth embodiments. FIG. 7B shows us its engaged state. In this model, trigger 7 used in the first embodiment is reintroduced. Spring 57 is attached between cylinder base 98 and piston 49. It is used to keep piston 49 stable at rest state and to bias it back from a charged or engaged state. Timer 95 is removed. In this case gas reservoir 5 has a volume equal to the sum of V1, V2, V3, V4 and V5 when it is charged with a compressed gas. The operational procedures are clear from the above description for a skilled in the art and will not be repeated either. Air tubes 60A-C are also introduced again. Such a configuration is easy to be produced more compact as trigger 7 does not need to be arranged coaxially with gas reservoir 5.

FIG. 8A shows a representation of a seventh embodiment—an inhaler 10 with an auto-feeding device at rest state. This model is modified from sixth embodiments. FIG. 8B shows us its engaged state. This is one preferable embodiment. In this model cylinder 61, piston 63, air tubes 60A-C and rubber ring gadget 64 of trigger 7 is removed so it is more compact than the sixth embodiment. Rod 66 works as trigger 7. In this case gas reservoir 5 has a volume equal to the sum of V1, V2, V4 and V5 when it is charged. The time delay or the time interval between the release of the compressed gas and the user's inhalation is equal to T1 plus T2 as described in the first embodiment. The operational procedures are clear from the above description for a skilled in the art and will neither be repeated here.

FIG. 9A shows a representation of an eighth embodiment—an inhaler 10 with auto-feeding device at rest state. This model is modified from seventh embodiments. FIG. 9B shows us its engaged state. This is another preferable embodiment. Cylinders 48 and 86 described above are part of a cylinder separated by a cylinder base 98A. Cylinder base 98A is inserted into a proper position in the cylinder. In this case cylinders 48 and 86 are defined as a pair of parallel cylinder. This embodiment is more compact and easier to produce than the last embodiment. The operational procedures are clear from the above description for a skilled in the art and will neither be repeated here.

FIG. 12A and FIG. 12B show us the sectional view of an alternative embodiment of piece 25 of drug feeder 2. In this embodiment, air channel 12F is a circular void having a predetermined diameter instead of a spiral conduit. Air channel 12E connects with 12F at an angle α, which ranges from 0 to 360 degree, preferably 80 to 100 degree. The most preferable α is 90 degree, which means that air channels 12E and 12F are preferably tangentially connected as shown in FIG. 12B. This configuration is easy to fabricate and also produce spiral airflow, or more precisely cyclone airflow, as air channel 12G is perpendicular to air channel 12E and is aligned coaxially with air channel 12F.

Accordingly, the reader will see that, according to the invention, I have provided active and suction actuated inhalers for delivering drug powders to a targeted area of a user's lung. They are simple, robust, easy-to-use, user- and environmental-friendly and universal. I should especially mention the use of a timer (8) to solve the problem of coordinating the drug powder dispersion and the user's inhalation. Another brilliant aspect of this invention is the use of the multifunction, volume changeable gas reservoir (5). It not only offers the source of the auxiliary energy in the form of a pressurized gas, but also acts as part of the timer (8), the trigger (7) and part of the drug feeder (2) via direct or indirect coupling mechanisms. It offers the driving force for the valve (9) to be automatically engaged and for the drug feeder (2) to automatically feed a unit dose of drug powder. It offers the core technology for the inhalers disclosed in this invention to be feature-rich whereas still relatively simple and compact. The other point of the invention is the use of the breath-actuated, or more precisely speaking the suction actuated trigger (3). By properly coupling the trigger (4) with the drug feeder (2), the user just needs to breath without worrying about feeding the drug wrong, as it is only opened after the drug powder properly fed. In combination with the timer (8) and the valve (9), the user's inhalation is fully used to deliver the aerosolised drug powder to the lung without being wasted on actuating a valve or a trigger. The other point of the invention is the drug feeder (2). By optimised design, the drug feeder not only feeds a unit dose of the drug powder but also offers the simple and effective way to entrain and to disperse the powder by using the integrated air channels (12E-G). The simple structure of coupling a dose counter (24) and a timer (94) to the drug feeding slide (20) makes the inhalers 10 richer in feature and more user friendly. The drug feeder (2) also offers a simple valve to the breath actuation air path (26A-D).

While the above description contains many specifications, these should not be construed as limitations on the scope of the invention, but as exemplifications of the presently preferred embodiments thereof. Many other ramifications and variations can be made without departing from the spirit and scope of the invention. Those having ordinary skill in the art will appreciate that various modifications can be made from the teaching of the invention. For examples:

Although the invention is described in detail with examples of dry powder inhalers, the basic devices and ideas can easily be adapted to a pressurized metered dose inhaler for a skilled in the art. It also is an easy task for a skilled in the art to insert a spacer between mouthpiece 1 and drug feeder 2 in such a case. It is also apparent for a skilled in the art that such a spacer can also be integrated into a dry powder inhaler so as to reduce the speed of the aerosolised drug particles.

Although the invention is described in detail with examples of (drug powder) reservoir based multi-dose dry powder inhalers, the basic devices and ideas can easily be adapted to a multiunit-doses inhaler for a skilled in the art. It will especially be an easy task for a skilled in the art to do such a modification with the multi-function cylinders mounted on a cylinder base.

It is obvious that drug-feeding slide 20 can also be a round rod, a ball, an oval rod or other shaped structure to delivery a dose of powder drug and at the same time to actuate dose counter 24, timer 94 and valve 23 etc.

Although a cylinder or a pair of parallel cylinder or a plurality of cylinders mounted on a cylinder base is used as the gas reservoir, other shaped containers whose effective volume for containing the compressed gas changes with the gas pressure can also be used for the same purpose.

It is also apparent for a skilled in the art that spiral air conduit 12F can also be a rod with rifling on its outside. In this case piece 25 of drug feeder 2 can easily be redesigned. For example, a drilling a hole at a proper position will be easily adapted to accommodate it.

Valves 4 and 9 can also use normal mechanical valves as the movements of rods 66, 66A and lever 43 can easily be adapted to actuate a valve other than a specially designed valve as disclosed in this invention. Valves 4 and 9 can also be electrical controlled ones that can easily be actuated by the relative movements of rod 66A and lever 43.

Triggers 3 and 7 can also be other forms of triggers such as those using an elastic flexible diaphragm. Dose counter 24 can also be an electrical one although a mechanical is preferred.

The rubber ring gadgets mounted on different pistons described in this disclosure can also be other sealing gadgets such as metal ones.

Check valves 54 and 83 can also be other kind of check valves. They are just given as examples in this invention for their simplicity.

Although a compressed gas is preferably used as an auxiliary energy for dispersing the drug powder, the mechanism disclosed in this invention can easily be adapted to actuate other auxiliary energies such as electrical powered vibration or a motored propeller etc.

The shape of the inhalers disclosed in this invention can be a traditional cylinder- or L- or T-shaped portable apparatus. They can also be made to fit into a box, an oval or a gun-like case.

The apparatus can also easily be adapted to other use such as a self-defending powder gun etc.

Air channel 12C can also be branched in such a manner that some branches connect mouthpiece 1 directly whereas others keep on going through air channels 12D and 12E. If necessary air channel 12C can directly connect with mouthpiece 1 without going through drug feeder 2.

Although most of the elements are made of metal, alloy, plastic and engineering plastic so as to reduce the cost, they can also be made of some expensive materials such as carbon fibre.

Further advantages of the inhaler are that it is operable to program the time interval between the drug dispersion and the user's inhalation. Therefore, the speeds of well-dispersed medicament particles in the aerosol are reduced, which in turn reduces the particles' impingement on to the surface of the user's mouth and throat. Hence, a higher percentage of medicament is delivered to the targeted region in the lung. By automatically timing the interval between the drug dispersion and the user's inhalation, the device also solves the long-suffered problem of developing an inhaler, ie how to make the user coordinate the drug dispersion with his or her inhalation easily and properly. The inhaler also solves a newly recognised problem of how to fully harness the user's inhalation for the delivery of a drug aerosol. The inhaler according to the invention is therefore very user-friendly and easy to use.

The inhaler is able to change the intensity and the total amount of the auxiliary energy that is used in a variety of ways, for example, the pressure of the pressurized air, and this may be adapted to an optimised value for different drug formulations. The inhaler is therefore versatile, and not limited to just one type of medicament. Also, the inhaler can easily change the interval between the drug dispersion and the user's inhalation so as to adapt an optimised value for any given drug formulation. The inhaler is therefore resourceful and user-friendly.

Furthermore, the inhaler can use suction to actuate the use of the auxiliary energy to aerosolise the medicament. The inhaler can therefore use the whole inhalation of the user to deliver a drug aerosol, and is therefore effective and easy to use. The inhaler can also automatically shut a valve controlling the intake of fresh air by the user upon increasing the auxiliary energy, such as a pressurized gas. The inhaler therefore does not waste any of the user's inhalation while suction-actuating the auxiliary energy. It is therefore easy to use.

The inhaler can feed the medicament from the reservoir, and so it has the so-called "multi-dosing ability", which is a significant advantage. Yet another advantage of the inhaler according to the invention is that it automatically couples the drug feed means and the suction-actuation air path in such a way that the suction-actuation air path is only open and ready for a user to inhale when the drug is fed properly.

Furthermore, the inhaler according to the invention is able to interlock the drug feeder with the charge of auxiliary energy, and also with the release mechanism of the auxiliary energy. All these advantages are maintained when the release mechanism of the auxiliary energy is controlled either automatically or manually.

Further objects and advantages of the inhaler, such as robustness and the fact that it is environmental-friendly will be apparent from a consideration of the specific description and drawings. Thus the scope of the invention should also (mainly) be determined by the appended claims and their legal equivalents, and not only by the examples given.

The invention claimed is:

1. An inhaler for dispensing medicament, the inhaler comprising:

- a gas container for containing compressed gas, the compressed gas being releasable from the gas container to aerosolise said medicament; and
- control means comprising a valve for controlling the passage of fresh air from the outside atmosphere to the user via a conduit;

said control means being configured to control a time interval between the aerosolisation of the medicament and the opening of the valve to allow the user's inhalation of fresh air from the outside atmosphere in response to a change in the volume and/or pressure of the gas in the gas container;

wherein the inhaler is operable, in use, to aerosolise the medicament using the compressed gas, and harness the user's inhalation of fresh air from the outside atmosphere to deliver the aerosolised medicament to the user by opening the valve after the time interval controlled by the control means; and wherein said compressed gas in said gas container can be released by means comprising:

a valve used to control an air channel, and a trigger, which can be actuated manually and/or by the user's suction force.

2. An inhaler for dispensing medicament, the inhaler comprising:

a gas container for containing compressed gas, the compressed gas being releasable from the gas container to aerosolise said medicament; and control means comprising a valve for controlling the passage of fresh air from the outside atmosphere to the user via a conduit;

a drug feeder that is actuated upon charging of said gas container;

said control means being configured to control a time interval between the aerosolisation of the medicament and the opening of the valve to allow the user's inhalation of fresh air from the outside atmosphere in response to a change in the volume and/or pressure of the gas in the gas container;

wherein the inhaler is operable, in use, to aerosolise the medicament using the compressed gas, and harness the user's inhalation of fresh air from the outside atmosphere to deliver the aerosolised medicament to the user by opening the valve after the time interval controlled by the control means; and wherein said drug feeder comprises a device that is used to measure a unit dose of drug powder from a powder reservoir.

3. A dry powder inhaler for dispensing medicament, the dry powder inhaler comprising:

a gas container for containing compressed gas, the compressed gas being releasable from the gas container to aerosolise said medicament; and control means comprising a valve for controlling the passage of fresh air from the outside atmosphere to the user via a conduit;

said control means being configured to control a time interval between the aerosolisation of the medicament and the opening of the valve to allow the user's inhalation of fresh air from the outside atmosphere in response to a change in the volume and/or pressure of the gas in the gas container;

wherein the dry powder inhaler is operable, in use, to aerosolise the medicament using the compressed gas, and harness the user's inhalation of fresh air from the outside atmosphere to deliver the aerosolised medicament to the user by opening the valve after the time interval controlled by the control means.

4. The inhaler according to claim 3, wherein the volume of the gas container is adapted to vary in response to a change in the pressure of the gas contained therein.

5. The inhaler according to claim 3, wherein the gas container comprises a piston slideably mounted therein, which piston is moveable between a first, "rest position" in which the volume of the container is at a first value when the pressure of gas in the container is at a first value, and a second, "engaged position", in which the volume of the container is at a second higher value when the pressure of gas in the container is at a second higher value.

6. The inhaler according to claim 3, wherein the piston is biased towards the first position.

7. The inhaler according to claim 3, further comprising;

a spiral gas conduit used to make spiral flow of said gas and/or air so as to entrain and to disperse said medicament effectively; or a cylinder cavity, where said medicament is, said gas and/or air being introduced via a gas channel at an optimised angle and exiting said cavity in a perpendicular direction so as to produce cyclone flow of said gas and/or air and hence to entrain and to disperse said medicament.

8. The inhaler according to claim 3, wherein the change in the volume and/or pressure of the gas in the gas container is detected by a sensor selected from a group comprising:

a piston that directly detects and responds to the changes in volume and/or pressure of said gas container; and a pressure gauge that can detect the change in pressure of said gas container.

9. The inhaler according to claim 3, wherein the control means is operable to control a time interval between the aerosolisation of the medicament and the user's inhalation, wherein the user's inhalation of fresh air only gets through into the user's mouth after aerosolisation has occurred for a certain time period.

10. The inhaler according to claim 3, wherein the control means comprises a timer.

11. The inhaler according to claim 10, wherein said timer is an inherent timer which is the combination effect of:

said gas container, a sensor or sensors, said valve, and a trigger which can be selected from a group comprising of: a cylinder with a piston having a attached rod; a cylinder with a diaphragm having a attached rod; other methods working as a trigger to open said valve;

whereby said sensor or sensors detect changes in said gas container, actuates said trigger to open said valve after a time interval so as to allow the fresh air going through the air channel for the user to inhale when said inhaler is in action.

12. A method of administering a dose of medicament to a subject, the method comprising the use of an inhaler according to claim 3.

* * * * *